US011123332B2

(12) United States Patent
Osten et al.

(10) Patent No.: US 11,123,332 B2
(45) Date of Patent: Sep. 21, 2021

(54) GABOXADOL FOR REDUCING RISK OF SUICIDE AND RAPID RELIEF OF DEPRESSION

(71) Applicant: Certego Therapeutics, Farmingdale, NY (US)

(72) Inventors: Pavel Osten, Brooklyn, NY (US); Kristin Baldwin, San Diego, CA (US)

(73) Assignee: Certego Therapeutics Inc., Framingham, NY (US)

( * ) Notice: Subject to any disclaimer, the term of this patent is extended or adjusted under 35 U.S.C. 154(b) by 0 days.

(21) Appl. No.: 16/691,049

(22) Filed: Nov. 21, 2019

(65) Prior Publication Data
US 2020/0155522 A1 May 21, 2020

Related U.S. Application Data

(60) Provisional application No. 62/770,287, filed on Nov. 21, 2018.

(51) Int. Cl.
*A61K 31/437* (2006.01)
*A61K 31/135* (2006.01)
*A61P 25/24* (2006.01)

(52) U.S. Cl.
CPC .......... *A61K 31/437* (2013.01); *A61K 31/135* (2013.01); *A61P 25/24* (2018.01)

(58) Field of Classification Search
CPC ...... A61K 31/437; A61K 31/135; A61P 25/24
See application file for complete search history.

(56) References Cited

U.S. PATENT DOCUMENTS

| | | | |
|---|---|---|---|
| 4,278,676 A | 7/1981 | Krogsgaard-Larsen | |
| 4,353,910 A | 10/1982 | Perregaard | |
| 4,362,731 A | 12/1982 | Hill | |
| 8,193,216 B2 | 6/2012 | Kumke et al. | |
| 9,744,159 B2 | 8/2017 | During | |
| 10,111,865 B2 | 10/2018 | During et al. | |
| 10,195,165 B2 | 2/2019 | During | |
| 2002/0165217 A1 | 11/2002 | Howard, Jr. | |
| 2004/0024038 A1 | 2/2004 | Ebert et al. | |
| 2005/0137222 A1 | 6/2005 | Ebert et al. | |
| 2005/0234093 A1 | 10/2005 | Sanchez et al. | |
| 2007/0287753 A1* | 12/2007 | Charney | A61K 9/0019 514/647 |
| 2007/0299048 A1 | 12/2007 | McKerman | |
| 2008/0159958 A1 | 7/2008 | Radek et al. | |
| 2008/0262029 A1 | 10/2008 | Crocker et al. | |
| 2009/0048288 A1 | 2/2009 | Ebert et al. | |
| 2009/0203731 A1 | 8/2009 | Sanchez et al. | |
| 2010/0093787 A1 | 4/2010 | Lundahl et al. | |
| 2011/0082171 A1 | 4/2011 | Ferguson et al. | |
| 2011/0301190 A1 | 12/2011 | Kumke et al. | |
| 2015/0313903 A1 | 11/2015 | During | |
| 2016/0228418 A1 | 8/2016 | During | |
| 2017/0020892 A1 | 1/2017 | Thompson et al. | |
| 2017/0119704 A1 | 5/2017 | During | |
| 2017/0246152 A1 | 8/2017 | During | |
| 2017/0296519 A1 | 10/2017 | During et al. | |
| 2017/0304358 A1 | 10/2017 | Ghaemi | |
| 2017/0319556 A1 | 11/2017 | During | |
| 2017/0348232 A1 | 12/2017 | During | |
| 2017/0348255 A1 | 12/2017 | During | |
| 2018/0065984 A1 | 3/2018 | De Faveri et al. | |
| 2018/0098974 A1 | 4/2018 | During | |
| 2018/0148380 A1 | 5/2018 | Eckel et al. | |
| 2018/0303805 A1 | 10/2018 | During | |
| 2018/0338959 A1 | 11/2018 | During | |
| 2018/0344709 A1 | 12/2018 | During | |
| 2018/0344745 A1 | 12/2018 | During | |
| 2019/0060400 A1 | 2/2019 | During | |
| 2019/0076415 A1 | 3/2019 | During | |
| 2019/0085358 A1 | 3/2019 | During | |
| 2019/0091209 A1 | 3/2019 | During | |
| 2019/0105308 A1 | 4/2019 | During | |
| 2019/0111033 A1 | 4/2019 | During | |
| 2019/0117632 A1 | 4/2019 | During | |
| 2019/0117633 A1 | 4/2019 | During | |

FOREIGN PATENT DOCUMENTS

| | | |
|---|---|---|
| AR | 105378 A1 | 9/2017 |
| AR | 105670 A1 | 10/2017 |
| BR | 112018004680 A2 | 9/2018 |
| CA | 2994952 A1 | 2/2017 |
| CN | 102137667 A | 7/2011 |
| CN | 107595850 A | 1/2018 |
| DE | 102005020882 A1 | 11/2006 |

(Continued)

OTHER PUBLICATIONS

Roose, S. P., "Depression, delusions, and suicide." Am J Psychiatry 140.9 (1983): 1159-1162.*
Friemel, A., "Postnatal development and kinetics of [3H] gaboxadol binding in rat brain: in vitro homogenate binding and quantitative autoradiography." Brain research 1170 (2007): 39-47.*
Jamie Sleigh, et al., "Ketamine—More Mechanisms of Action than Just NMDA Blockade," Trends in Anaesthesia and Critical Care, 2014, pp. 76-81, 4.
E. Roberts, et al., "The Evidence for Lithium in Suicide Prevention," The British Journal of Psychiatry, 2017, p. 396, 211.
J.K. Rybakowski, et al., "Excellent Lithium Responders Have Normal Cognitive Functions and Plasma BDNF Levels," International Journal of Neuropsychopharmacology, 2010, pp. 617-622, 13.
Soren Korsgaard, et al., "The Effect of Tetrahydroisoxazolopyridinol (THIP) in Tardive Dyskinesia: a New Gamma-aminobutyric Acid Agonist," Arch. Gen. Psychiatry, 1982, pp. 1017-1021, 39.
G. Sani, et al., "Treatment of Bipolar Disorder in a Lifetime Perspective: Is Lithium Still the Best Choice?," Clinical Drug Investigation, 2017, pp. 713-727, 37.

(Continued)

*Primary Examiner* — John M Mauro
(74) *Attorney, Agent, or Firm* — Gearhart Law LLC

(57) ABSTRACT

Methods and compositions are disclosed for rapidly reducing the risk of suicide in patients suffering from acute suicidality and rapidly relieving mood symptoms in major depression and treatment-resistant depression using a novel therapeutic regimen comprising a single or intermittent administration of a high dose of gaboxadol, or a pharmaceutically acceptable salt thereof, to the subject n need thereof.

58 Claims, 6 Drawing Sheets

(56) References Cited

FOREIGN PATENT DOCUMENTS

| | | |
|---|---|---|
| EA | 007287 B1 | 8/2006 |
| EA | 200300594 A1 | 8/2006 |
| EP | 0000338 B1 | 11/1981 |
| EP | 0840601 B1 | 10/2001 |
| EP | 1337247 A1 | 8/2003 |
| EP | 2145620 A3 | 3/2010 |
| ME | 00030 B | 6/2010 |
| MX | 2018001720 A | 9/2018 |
| NZ | 565880 A | 7/2011 |
| NZ | 623341 A | 4/2016 |
| PT | 1641456 E | 6/2010 |
| TW | 200501951 A | 1/2005 |
| TW | 200924757 A | 6/2009 |
| UA | 90656 C2 | 5/2010 |
| UA | 91496 C2 | 8/2010 |
| WO | 2004112786 A2 | 12/2004 |
| WO | 2005073237 A3 | 10/2005 |
| WO | 2005094820 A1 | 10/2005 |
| WO | 2009021521 A2 | 2/2009 |
| WO | 2017015049 A1 | 1/2017 |
| WO | 2017027249 A1 | 2/2017 |
| WO | 2019006161 A1 | 1/2019 |
| WO | 2019028234 A1 | 2/2019 |
| WO | 2019055369 A1 | 3/2019 |
| WO | 2019195813 A1 | 10/2019 |
| ZA | 200607427 B | 2/2009 |

OTHER PUBLICATIONS

M. Schou, et al., "Lithium Poisoning," American Journal of Psychiatry, 1968, pp. 520-527, 125.
J. Scott, et al., "Cross-validation of Clinical Characteristics and Treatment Patterns Associated with Phenotypes for Lithium Response Defined by the Alda Scale," Journal of Affective Disorders, 2017, pp. 62-67, 208.
David Nutt, et al., "Differences Between Magnetoencephalographic (MEG) Spectral Profiles of Drugs Acting on GABA at Synaptic and Extrasynaptic Sites: A Study in Healthy Volunteers," Neuropharmacology, 2015, pp. 155-163, 88.
E. Severus, et al., "Lithium for Prevention of Mood Episodes in Bipolar Disorders: Systematic Review and Meta-Analysis," International Journal of Bipolar Disorders, 2014, p. 15, 2.
L.K. Singh, et al., "Improving Tolerability of Lithium with a Once-Daily Dosing Schedule," American Journal of Therapeutics, 2011, pp. 288-291, 18.
Jonas Lundahl, et al., "EEG Spectral Power Density Profiles During NREM Sleep for Gaboxadol and Zolpidem in Patients with Primary Insomnia," Journal of Psychopharmacology, 2012, pp. 1081-1087, 26(8).
Povl Krogsgaard-Larsen, et al., "Deuterium Labelling of the GABA Agonists THIP, Piperidine-4-sulphonic Acid and the GABA Uptake Inhibitor THPO," Journal of Labelled Compounds and Radiopharmaceuticals, 1982, pp. 689-702, vol. XIX, No. 5.
J. Tiihonen et al., "Real-World Effectiveness of Pharmacological Treatments in Severe Unipolar Depression in a Nationwide Cohort of 123,712 Patients," American College of Neuropsychopharmacology, 2016.
E. Toffol, et al., "Lithium is Associated with Decrease in All-Cause and Suicide Mortality in High-Risk Bipolar Patients: A Nationwide Registry-Based Prospective Cohort Study," Journal of Affective Disorders, 2015, pp. 159-165, 183.
A. Vita, et al., "Lithium in Drinking Water and Suicide Prevention: A Review of the Evidence," International Clinical Psychopharmacology, 2015, pp. 1-5, 30.
R. Wesseloo, et al., "Lithium Dosing Strategies During Pregnancy and the Postpartum Period," The British Journal of Psychiatry, 2017, pp. 31-36, 211.
E. Won, et al., "An Oldie But Goodie: Lithium in the Treatment of Bipolar Disorder Through Neuroprotective and Neurotrophic Mechanisms," International Journal of Molecular Sciences, 2017, p. 2679, 18.

D.J. Dijk, et al., "Sex Differences and the Effect of Gaboxadol and Zolpidem on EEG Power Spectra in NREM and REM Sleep," Journal of Psychopharmacology, 2010, pp. 1613-1618, 24(11).
J.W. Murrough, et al., "Ketamine for Rapid Reduction of Suicidal Ideation: A Randomized Controlled Trial," Psychological Medicine, 2015, pp. 3571-3580, 45.
H.M. Emrich, et al., "Therapeutic Effects of GABA-ergic Drugs in Affective Disorders: A Preliminary Report," Pharmacology Biochemistry & Behavior, 1983, pp. 369-372, 19.
Michael F. Grunebaum, et al., "Ketamine for Rapid Reduction of Suicidal Thoughts in Major Depression: A Midazolam-Controlled Randomized Clinical Trial," Am. J. Psychiatry, 2018, pp. 327-335, 175(4).
Rudolf Hoehn-Saric, "Effects of THIP on Chronic Anxiety," Psychopharmacology, 1983, pp. 338-341, 80.
Written Opinion of the International Searching Authority, dated Feb. 4, 2020, for corresponding PCT Application No. PCT/US19/62554, filed Nov. 21, 2019, consisting of 6 Pages.
International Search Report, dated Feb. 4, 2020, for corresponding PCT Application No. PCT/US19/62554, filed Nov. 21, 2019, consisting of 2 Pages.
Cao, Z., et al., "Identifying Ketamine Responses in Treatment-Resistant Depression Using a Wearable Forehead EEG," IEEE Transcations on Biomedical Engineering, vol. 66, Issue 6, Jun. 2019.
Domschke, K., et al., "Magnetoencephalographic Correlates of Emotional Processing in Major Depression Before and After Pharmacological Treatment," International Journal of Neuropsychopharmacology, 2015.
Written Opinion of the International Searching Authority, dated Jan. 27, 2020, for corresponding PCT Application No. PCT/US19/62644, filed Nov. 21, 2019, consisting of 10 Pages.
International Search Report, dated Jan. 27, 2020, for corresponding PCT Application No. PCT/US19/62644, filed Nov. 21, 2019, consisting of 3 Pages.
Engber, T. M., et al., "Differential Patterns of Regional C-Fos Induction in the Rat Brain by Amphetamine and the Novel Wakefulness-promoting Agent Modafinil," Neuroscience Letters, 1998, pp. 95-98, 241 (2-3).
Herrera, D. G., et al., "Activation of C-Fos in the Brain," Progress in Neurobiology, Oct. 1996, pp. 83-107, 50 (2-3).
A. Kiss, "C-Fos Expression in the Hypothalamic Paraventricular Nucleus After a Single Treatment with a Typical Haloperidol and Nine Atypical Antipsychotics: A Pilot Study," Endocrine Regulations, 2018, pp. 93-100, 52(2).
N. Renier, et al., "Mapping of Brain Activity by Automated Volume Analysis of Immediate Early Genes," Cell, 2016, pp. 1789-1802, 165(7).
O. Salminen, et al., "Expression of Fos Protein in Various Rat Brain Areas Following Acute Nicotine and Diazepam," Pharmacology Biochemistry and Behavior, 1996, pp. 241-248, 54(1).
J. I. Semba, et al., "Differential Expression of C-Fos mRNA in Rat Prefrontal Cortex, Striatum, N. Accumbens and Lateral Septum After Typical and Atypical Antipsychotics: an In Situ Hybridization Study," Neurochemistry International, 1996, pp. 435-442, 29(4).
D. A. Slattery, et al., "Comparison of Alterations in C-fos and Egr-1 (zif268) Expression Throughout the Rat Brain Following Acute Administration of Different Classes of Antidepressant Compounds," Neuropsychopharmacology, 2005, p. 1278, 30(7).
B. E. Sumner, et al., "Testing the Validity of C-fos Expression Profiling to Aid the Therapeutic Classification of Psychoactive Drugs," Psychopharmacology (Berl), 2004, pp. 306-321, 171(3).
M. T. Abou-Saleh, "Lithium in the Episode and Suicide Prophylaxis and in Augmenting Strategies in Patients with Unipolar Depression," International Journal of Bipolar Disorders, 2017, p. 11, 5.
S. Ando, et al., "Lithium Levels in Tap Water and the Mental Health Problems of Adolescents: An Individual-Level Cross-Sectional Survey," The Journal of Clinical Psychiatry, 2017, pp. e252-e256, 78.
M. Andrade Nunes, et al., "Microdose Lithium Treatment Stabilized Cognitive Impairment in Patients with Alzheimer's Disease," Current Alzheimer Research, 2013, pp. 104-107, 10.
A. P. Association, "Practice Guideline for the Treatment of Patients with Bipolar Disorder," American Psychiatric Pub., 2002.

(56) References Cited

OTHER PUBLICATIONS

R. J. Baldessarini, et al., "Decreased Risk of Suicides and Attempts During Long-Term Lithium Treatment: A Meta-Analytic Review," Bipolar Disorders, 2006, pp. 625-639, 8.

R. J. Baldessarini, et al., "Lithium Treatment and Suicide Risk in Major Affective Disorders: Update and New Findings," Journal of Clinical Psychiatry, 2003, pp. 44-52, 64.

U. Berggren, et al., "The Effect of Lithium on Amphetamine-Induced Locomotor Stimulation," Psychopharmacology, 1978, pp. 41-45, 59.

G. Bersani, et al., "Potential Neuroprotective Effect of Lithium in Bipolar Patients Evaluated by Neuropsychological Assessment: Preliminary Results," Human Psychopharmacology: Clinical and Experimental, 2016, pp. 19-28, 31.

P. Cappeliez, et al., "Effects of Lithium on an Amphetamine Animal Model of Bipolar Disorder," Progress in Neuro-Psychopharmacology and Biological Psychiatry, 1990, pp. 347-358, 14.

L. Carter, et al., "An Updated Review of the Optimal Lithium Dosage Regiment for Renal Protection," The Canadian Journal of Psychiatry, 2013, pp. 595-600, 58.

A. Cipriani, et al., "Lithium in the Prevention of Suicide in Mood Disorders: an Updated Systematic Review and Meta-Analysis," The BMJ, 2013, p. f3646, 346.

A. Cipriani, et al., "Lithium in the Prevention of Suicidal Behavior and All-Cause Mortality in Patients with Mood Disorders: a Systematic Review of Randomized Trials," American Journal of Psychiatry, 2005, pp. 1805-1819, 162.

J. Davis et al., "Lithium and Nephrotoxicity: a Literature Review of Approaches to Clinical Management and Risk Stratification," BMC Nephrology, 2018a, p. 305, 19.

J. Davis et al., "Lithium and Nephrotoxicity: Unraveling the Complex Pathophysiological Threads of the Lightest Metal," Nephrology, 2018b, pp. 897-903, 23.

K. M. Deligiannidis, et al., "Pharmacotherapy for Mood Disorders in Pregnancy: a Review of Pharmacokinetic Changes and Clinical Recommendations for Therapeutic Drug Monitoring," Journal of Clinical Psychopharmacology, 2014, p. 244, 34.

N. Dunn, et al., "Does Lithium Therapy Protect Against the Onset of Dementia?," Alzheimer Disease & Associated Disorders, 2005, pp. 20-22, 19.

S. Rej, et al., "Lithium Dosing and Serum Concentrations Across the Age Spectrum: From Early Adulthood to the Tenth Decade of Life," Drugs & Aging, 2014, pp. 911-916, 31.

A.J. Gelenberg, et al., "Comparison of Standard and Low Serum Levels of Lithium for Maintenance Treatment of Bipolar Disorder," New England Journal of Medicine, 1989, pp. 1489-1493, 321.

E.M. Grandjean, et al., "Lithium: Updated Human Knowledge Using an Evidence-Based Approach: Part III: Clinical Safety," CNS Drugs, 2009, pp. 397-418, 23.

S. Horton, et al., "Maximum Recommended Dosage of Lithium for Pregnant Women Based on a PBPK Model for Lithium Absorption," Advances in Bioinformatics, 2012.

S.P. Hunt, et al., "Induction of C-Fos-like Protein in Spinal Cord Neurons Following Sensory Stimulation," Nature, 1987, pp. 632-634, 328(6131).

A. Ivkovic, et al., "Lithium-induced Neurotoxicity: Clinical Presentations, Pathophysiology, and Treatment," Psychosomatics, 2014, 55, 296.

S. Jain et al., "From Single Genes to Gene Networks: High-throughput-high-content Screening for Neurological Disease," Neuron, 2010, pp. 207-217, 68.

M.S. Judenhofer, et al., "Simultaneous PET-MRI: a New Approach for Functional and Morphological Imaging," Nature Medicine, 2008, pp. 459-465, 14.

T. Kato, et al., "Animal Models of Bipolar Disorder," Neuroscience & Biobehavioral Reviews, 2007, pp. 832-842, 31.

L.V. Kessing, et al., "Effectiveness of Maintenance Therapy of Lithium vs Other Mood Stabilizers in Monotherapy and in Combinations: a Systematic Review of Evidence from Observational Studies," Bipolar Disorders, 2018, pp. 419-431, 20.

L.V. Kessing, et al., "Does Lithium Protect Against Dementia?," Bipolar Disorders, 2010, pp. 87-94, 12.

D. Ljubicic, et al., "Lithium Treatments: Single and Multiple Daily Dosing," the Canadian Journal of Psychiatry, 2008, pp. 323-331, 53.

B. Madhusudham, "Nonconvulsive Status Epilepticus and Creutzfeldt-Jakob-like EEG Changes in a Case of Lithium Toxicity," Epilepsy & Behavior Case Reports, 2014, pp. 203-205, 2.

A. Markou, et al., "Removing Obstacles in Neuroscience Drug Discovery: the Future Path for Animal Models," Neuropsychopharmacology, 2009, pp. 74-89, 34.

B. Megarbane, et al., "Lithium-related Neurotoxicitiy Despite Serum Concentrations in the Therapeutic Range: Risk Factors and Diagnosis," Shanghai Archives of Psychiatry, 2014, 26, 243.

L. Oehlund, et al., "Reasons for Lithium Discontinuation in Men and Women with Bipolar Disorder: A retrospective Cohort Study," BMC Psychiatry, 2018, p. 37, 18.

F. Pammolli, et al., "The Productivity Crisis in Pharmaceutical R&D," Nat. Rev. Drug Discovery, 2011, pp. 428-438, 10.

R. M. Post, "The News News About Lithium: An Underutilized Treatment in the United States," Neuropsychopharmacology, 2018, p. 1174, 43.

A. Quartini, et al., "Lithium: From Mood Stabilizer to Putative Cognitive Enhancer," Neural Regeneration Research, 2016, p. 1234, 11.

Dawn F. Ionescu, et al., "Current Trends in Identifying Rapidly Acting Treatments for Depression," Curr. Behav. Neurosci. Rep., 2016, pp. 185-191, 3(2).

Kaspar et al "Combining Escitalopram With Gaboxadol Provides no Additional Benefit in the Treatment of Patients With Severe Major Depressive Disorder", Int J Neuropsychopharmacol. Jul. 2012;15(6):715-25 [Retrieved from internet Nov. 13, 2020] https://pubmed.ncbi.nlm.nih.gov/22008735/.

Lundbeck study ClinicalTrials.gov Identifier: NCT00807248, [Retrieved from internet Nov. 13, 2020] https://clinicaltrials.gov/ct2/show/NCT00807248.

Hammad, T. A., et al., 2006, "Suicidality in pediatric patients treated with antidepressant drugs." Archives of general psychiatry 63(3): 332-339 [Retrieved from internet Nov. 13, 2020] https://jamanetwork.com/journals/jamapsychiatry/fullarticle/209399.

Meltzer, H. Y. et al., 2003. "Clozapine treatment for suicidality in schizophrenia: international suicide prevention trial (InterSePT)." Archives of general psychiatry 60(1): 82-9 [Retrieved from internet Nov. 13, 2020] https://pubmed.ncbi.nlm.nih.gov/12511175/.

ClinicalTrial: NCT02094898; Dadiomov, D. and K. Lee, 2019, "The effects of ketamine on suicidality across various formulations and study settings." Mental Health Clinician 9(1): 48-60 [Retrieved from internet Nov. 13, 2020] https://clinicaltrials.gov/ct2/show/NCT02094898.

Mann, J. J. ,2003,. "Neurobiology of suicidal behavior." Nature Reviews Neuroscience 4(10): 819-828.

Oquendo, M. A., E. et al., 2008, Issues for DSM-V: suicidal behavior as a separate diagnosis on a separate axis, Am Psychiatric Assoc [Retrieved from internet Nov. 13, 2020] https://ajp.psychiatryonline.org/doi/10.1176/appi.ajp.2008.08020281.

Association, A. P., 2013, Diagnostic and statistical manual of mental disorders (DSM-5®), American Psychiatric Pub.

Norman L. Foster, et al., "THIP Treatment of Huntington's Disease," Neurology, May 1, 1983, pp. 637-639, 33(5).

Rudolf Hoehn-Saric, "Effects of THIP on Chronic Anxiety," Psychopharmacology, Jul. 1983, pp. 338-341, 80.

Søren Korsgaard et al., "The Effect of Tetrahydroisoxazolopyridinol (THIP) in Tardive Dyskinesia: A New β-Aminobutyric Acid Agonist," Archives of General Psychiatry, Sep. 1982, pp. 1017-1021, 39(9).

E. Mohr, et al., "GABA-agonist Therapy for Alzheimer's disease," Clinical Neropharmacology, 1986, pp. 257-266. 9(3).

K. Mondrup, et al., "The acute Effect of the GABA-Agonist, THIP, on Propriceptive and Flexor Reflexes in Spastic Patients," Acta Nerologica Scandinavica, 1983, pp. 48-54, 67.

Thomas Roth, et al., "Effect of Gaboxadol on Patient-Reported Measures of Sleep and waking Function in Patients with Primary

(56) References Cited

OTHER PUBLICATIONS

Insomnia: Results From two Randomized, Controlled, 3-Month Studies," Journal of Clinical Sleep Medicines, Feb. 2021, pp. 30-39, 6(1).

* cited by examiner

FIGURE 1: METHOD FOR WHOLE-BRAIN PHARMACOMAPS REPRESENTING DRUG-EVOKED BRAIN ACTIVATION IN THE MOUSE.

FIGURE 2: KETAMINE DOSE-CURVE PHARMACOMAPS.

FIGURE 3: GABOXADOL AND KETAMINE SIDE-BY-SIDE PHARMACOMAP COMPARISON

FIGURE 4: SYNERGISTIC EFFECT OF CO-APPLICATION OF GABOXADOL AND KETAMINE AT SUB-THRESHOLD DOSES

FIGURE 5: FORCED SWIM TEST

GABOXADOL FOR REDUCING RISK OF SUICIDE AND RAPID RELIEF OF DEPRESSION

CROSS-REFERENCE TO RELATED APPLICATIONS

This application claims priority to Provisional Patent Application No. 62/770,287 filed on Nov. 21, 2018, the content of which is incorporated by reference herein in their entirety.

FIELD OF THE EMBODIMENTS

This invention relates to methods and compositions for rapidly reducing the risk of suicide in patients suffering from acute suicidality and rapidly relieving mood symptoms in major depression and treatment-resistant depression using a novel therapeutic regimen comprising a single or intermittent administration of a high dose of gaboxadol, or a pharmaceutically acceptable salt thereof, to the subject in need thereof.

BACKGROUND OF THE EMBODIMENTS

According to the World Health Organization, depression is the leading cause of disability and ill health in the world affecting more than 300 million people worldwide and costing the global economy an estimated $1 trillion in lost productivity each year. The Centers for Disease Control (CDC) estimate that in the U.S. alone, 20-25% of all adults aged 18 and older and 10.9% of young adults aged 18-25 experience at least one episode of major depression each year. Left untreated, mental diseases, like major depression, are a major contributor to suicide in the U.S which takes the lives of more than 47,000 Americans every year or one death by suicide every 11 minutes (Shepard et al., Suicide Life Threat Behav. (2016) 46(3)352-62.). There is one suicide for every estimated 25 suicide attempts which means each year there are an estimated quarter million people who become suicide survivors. Hence, there is a critical unmet need for rapid-acting medications for the treatment of suicidal ideation and treatment-resistant depression (TRD).

Recently, esketamine (Spravato) delivered intranasally has been approved by the US Food and Drug Administration (FDA) as the first rapid acting antidepressant, bringing hope to patients with TRD and acute suicidal ideation (Bahr et al., 2019; Pochwat et al., 2019). Esketamine indeed shows a remarkably rapid efficacy, with positive therapeutic effects seen with a day or only a few days post dosing, in contrast to traditional antidepressants that take weeks to achieve efficacy (Krystal et al., 2019, Neuron 101, 774-778; Harmer et al., 2009; The British Journal of Psychiatry 195, 102-108; Uher et al., 2010, Psychological Medicine 40, 1367-1377). However, esketamine is also associated with significant side effects, including psychosis-like psychotomimetic side effects with delusions and delirium and drug abuse liability. The psychotomimetic side effects are of a particular concern in TRD and suicidal patients and therefore Spravato can be only administered in doctor's office where patients must be monitored by a health professional for at least 2 hours post dose. Therefore there is a continuing need for the development of safer therapeutic options with similar rapid efficacy as esketamine. Gaboxadol or THIP (4,5,6,7-tetrahydroisoxazolo (5,4-c) pyridin-3-ol) is a selective GABAA receptor agonist with a preference for δ-subunit containing GABAA receptors. In the early 1980s gaboxadol was the subject of a series of pilot studies that tested its efficacy as an analgesic and anxiolytic, as well as a treatment for tardive dyskinesia, Huntington's disease, Alzheimer's disease (Mohr, Bruno et al. Clin Neuropharmacol. 1986; 9(3):257-63), and spasticity. In the 1990s gaboxadol moved into late stage development for the treatment of insomnia. The development was discontinued after the compound failed to show significant effects in sleep onset and sleep maintenance in a three-month efficacy study. (Methods of treating depression with low doses of gaboxadol are disclosed in WO2004112786, which is incorporated by reference herein in its entirety. A clinical trial to investigate the efficacy of gaboxadol in the treatment of symptoms of Angelman Syndrome (a developmental disorder) sponsored by Ovid Therapeutics Inc. (ClinicalTrials.gov Identifier: NCT02996305) is currently underway (Cogram, Deacon et al. 2019). Patent applications on related subject matter include U.S. Pat. No. 9,744,159, published US Patent Application No. 2017/348232 and WIPO International Patent Application WO2017015049, the contents of which are incorporated herein by reference in their entireties.

Methods of treating depression with low doses of gaboxadol are disclosed in WO2004112786, which is incorporated by reference herein in its entirety.

A clinical trial by Lundbeck reported at ClinicalTrials.gov Identifier: NCT00807248 treated 490 patients with daily oral doses of escitalopram (20 mg) and gaboxadol (5 mg or 10 mg). The trial found that oral gaboxadol at this amount provided no additional benefit in the treatment of patients with severe major depressive disorder. A report on this trial is found at Kaspar et al (2012) Int J Neuropsychopharmacol. 2012 July; 15(6):715-25. test for effects on patients diagnosed with suicidal ideation or identified as at risk of suicide. The trial also did not test the effect of gaboxadol alone.

Gaboxadol (4,5,6,7-tetrahydroisoxazolo [5,4-c]pyridine-3-ol) (THIP)) is also described in EP Patent No. 0000338 and in EP Patent No. 0840601, U.S. Pat. Nos. 4,278,676, 4,362,731, 4,353,910, and WO 2005/094820, the contents of which are hereby incorporated by reference herein in their entireties.

None of the art described above addresses the urgent treatment of patients suffering from acute suicidality and treatment-resistant depression by administering a high dose (e.g., >50 mg per dose) gaboxadol once or intermittently every three days or more.

SUMMARY OF THE EMBODIMENTS

Methods of reducing risk of suicide and/or achieving rapid relief of depression symptoms described herein include administering to a patient in need thereof an amount of gaboxadol or a pharmaceutically acceptable salt thereof sufficient to reduce the risk of suicide. Methods of reducing risk of suicide and achieving rapid relief from depression described herein include administering to a patient in need thereof a first single dose treatment of about 50 mg to about 300 mg gaboxadol or a pharmaceutically acceptable salt thereof wherein the first treatment provides improvement in the patient within 1 day and for 3 or more days after administration to the patient. No gaboxadol in any form is administered to the patient for 3 or more days following the first treatment after reaching a therapeutic effect threshold based on one or more clinical biomarkers, such as EEG or blood level of gaboxadol.

The first treatment of gaboxadol comprises an initial administration of gaboxadol or a pharmaceutically acceptable salt thereof and optionally, additional administration(s) of gaboxadol, or a pharmaceutically acceptable salt thereof, within 12 hours immediately following the initial administration. The optional second administration may be administered if a clinical test of the patient demonstrates insufficient response in the 160 minutes immediately after the first administration. In one embodiment, the insufficient response is an EEG power density increase of less than 30% at the time point 160 minutes after the first administration. The EEG power density is preferably calculated in the 4.75-8.0 Hz range. Alternatively, the insufficient response may be a whole head MEG planar gradiometer increase of less +3 in the combined delta, theta and alpha activity at the time point 160 minutes after the first administration. The additional administration comprises gaboxadol up to the remainder of the maximum total first treatment dose of 300 mg. Insufficient response may also mean failure to achieve a specified blood level of gaboxadol.

Methods of reducing risk of suicide and achieving a rapid relief from depression are described herein which include administering to a patient in need thereof gaboxadol or a pharmaceutically acceptable salt thereof wherein the method provides an in vivo plasma profile including a $C_{max}$ greater than about 900 ng/ml wherein the method provides rapid improvement in the patient after administration of the gaboxadol or a pharmaceutically acceptable salt thereof. Methods of reducing risk of suicide and achieving a rapid relief from depression described herein include administering to a patient in need thereof gaboxadol or a pharmaceutically acceptable salt thereof wherein the method provides an in vivo plasma profile comprising an $AUC_{0-2}$ of greater than about 900 ng*hr/ml and wherein the method provides rapid improvement in the patient after administration of the gaboxadol or a pharmaceutically acceptable salt thereof.

A method for reducing an imminent risk of suicide in a patient suffering from acute suicidality is disclosed comprising administering a single dose 50 to 300 mg gaboxadol, or pharmaceutically acceptable salt thereof, to the patient, wherein the dose reduces the incidence of suicidal ideation within 24 hours of the administration.

Methods of reducing risk of suicide and achieving a rapid relief from depression are described herein which include administering to a patient in need thereof a first pharmaceutical composition comprising gaboxadol or a pharmaceutically acceptable salt thereof and a second pharmaceutical composition comprising ketamine, SAGE-217, tiagabine, clozapine and pharmaceutically acceptable salts thereof. In certain embodiments, gaboxadol and ketamine are each provided at a synergistic dose, and may optionally be administered at the same time.

A method for reducing a risk of suicide and/or achieving a rapid-acting relief of depressive symptoms is disclosed comprising administering, a first treatment of gaboxadol, or pharmaceutically acceptable salt thereof, to a patient in need thereof in an amount sufficient to reduce the risk of suicide and/or to rapidly alleviate depressive symptoms, and optionally, administering a second treatment of gaboxadol, or pharmaceutically acceptable salt thereof, within less than 6 hours immediately following the administration of the first treatment, and if the patient experiences a recurrence of the risk of suicide and/or depressive symptoms, administering an additional treatment of gaboxadol, or pharmaceutically acceptable salt thereof, but not until at least 48 hours after the first treatment.

In certain embodiments, the additional treatment of gaboxadol, or pharmaceutically acceptable salt thereof, is administered at least every 3, 4, 5, 6 or 7 days after the administration of the first treatment.

In certain embodiments, the second treatment of gaboxadol, or pharmaceutically acceptable salt thereof, is administered if a neurological test of the patient demonstrates an insufficient response within 180 minutes immediately after administration of the first treatment.

In certain embodiments, the insufficient response is an electroencephalogram (EEG) power density increase of less than 30% over baseline within 180 minutes after the first administration or a whole head magnetoencephalography (MEG) planar gradiometer increase of less +3 in a combined delta, theta and alpha activity within 180 minutes after the administration of the first treatment.

In certain embodiments, the electroencephalogram (EEG) power density is calculated in a 0.25-8.0 Hz range or in a 4.75-8.0 Hz range.

In certain embodiments, the electroencephalogram (EEG) power density is calculated in a Sigma (11.5-15.0 Hz), Beta-1 (15.5-20.0 Hz), Beta-2 (20.5-25.0 Hz) or Beta-3 (25.5-32.0 Hz) range.

In certain embodiments, the second treatment of gaboxadol, or pharmaceutically acceptable salt thereof, is administered if a neurological test of the patient demonstrates an insufficient response within about 30, 60, 90 or 120 minutes immediately after administration of the first treatment.

In certain embodiments, the insufficient response is an electroencephalogram (EEG) power density increase of less than 30% over baseline within 180 minutes after the first administration or a whole head magnetoencephalography (MEG) planar gradiometer increase of less +3 in a combined delta, theta and alpha activity within about 30, 60, 90 or 120 minutes after the administration of the first treatment.

In certain embodiments, the method provides improvement in at least one symptom of risk of suicide selected from the group consisting of suicidal ideation, acute suicidality, recurrent thoughts of death, actions towards suicide and/or suicide attempts.

In certain embodiments, the patient is further diagnosed with a condition selected from among suicidal ideation, acute suicidality, risk of self-harm and/or treatment-resistant depression.

In certain embodiments, the patient has not been previously treated with, or is not currently being treated with, or is not responding to, an anti-depressive treatment.

In certain embodiments, the administration of the first treatment comprises about 1 mg to about 300 mg gaboxadol or a pharmaceutically acceptable salt thereof.

In certain embodiments, the administration of the first treatment comprises about 33 mg to about 300 mg gaboxadol or a pharmaceutically acceptable salt thereof.

In certain embodiments, the administration of the first treatment comprises about 50 mg to about 300 mg gaboxadol or a pharmaceutically acceptable salt thereof.

In certain embodiments, the administration of the first treatment comprises about 33 mg to about 50 mg gaboxadol or a pharmaceutically acceptable salt thereof.

In certain embodiments, the administration of the first treatment comprises about 50 mg to about 150 mg gaboxadol or a pharmaceutically acceptable salt thereof.

In certain embodiments, the first treatment is administered in an oral dosage form.

In certain embodiments, the oral dosage form is an orally disintegrating form.

In certain embodiments, the first treatment is administered intranasally.

In certain embodiments, the administration of the first treatment of gaboxadol, or pharmaceutically acceptable salt thereof, results in a blood level that exceeds a $GABA_A$ receptor saturation level.

In certain embodiments, the $GABA_A$ receptor saturation level is a blood level greater than 900 ng/ml.

In certain embodiments, a patient's plasma level of gaboxadol achieves $AUC_{0-2}$ of greater than about 900 ng*hr/ml after the administration of the first treatment.

In certain embodiments, a plasma $T_{max}$ of gaboxadol is achieved within 45 minutes after administration of the first treatment.

In certain embodiments, the method further comprises administering to the patient, before after or concurrently with the first treatment, any one of ketamine, SAGE-217, allopregnanolone, ganaxolone, alfadolone, alfaxolone, hydroxydione, minaxolone, pregnanolone, renanolone and other pregnane neurosteroids, AV-101 (L-4-Chlorokynurenine), rapastinel (GLYX-13), MGS0039, LY-341,495, MK-801 (dizocilpine), Ro 25-6981, rislenemdaz (CERC-301, MK-0657), apimostinel (NRX-1074), lanicemine (AZD6765), traxoprodil (CP-101606), (2R,6R)-hydroxynorketamine, decoglurant (INN) (RG1578, RO4995819), memantine, tiagabine, clozapine, [2-amino-4-(2,4,6-trimethylbenzylamino)-phenyl]carbamic acid ethyl ester (AA29504) and pharmaceutically acceptable salts thereof.

In certain embodiments, the first treatment comprises administering concurrently a synergistic dose of gaboxadol, or pharmaceutically acceptable salt thereof, together with a synergistic dose of ketamine wherein the synergistic dose of gaboxadol, or pharmaceutically acceptable salt thereof, can be about 20 mg or less and the synergistic dose of ketamine can be about 10 mg or less.

In certain embodiments, the synergistic dose of gaboxadol, or pharmaceutically acceptable salt thereof, can be about 20 mg, about 19 mg, about 18 mg, about 17 mg, about 16 mg, about 15 mg, about 14 mg, about 13 mg, about 12 mg, about 11 mg, about 10 mg, about 9 mg, about 8 mg, about 7 mg, about 6 mg, about 5 mg, about 4 mg, about 3 mg, about 2 mg, about 1 mg or less.

In certain embodiments, synergistic dose of ketamine can be about 10 mg can be about 10 mg, about 9 mg, about 8 mg, about 7 mg, about 6 mg, about 5 mg, about 4 mg, about 3 mg, about 2 mg, about 1 mg or less.

A use of gaboxadol is disclosed for reducing risk of suicide in a patient at risk of suicide and/or for achieving fast-acting relief of depressive symptoms.

A use of gaboxadol is disclosed for the manufacture of a medicament for reducing risk of suicide in a patient at risk of suicide and/or achieving fast-acting relief of depressive symptoms.

White color indicates the spatial areas of significant drug-evoked activation. The very broad activation pattern evoked by ketamine at 10 mg/kg included the following anatomical structures:
Cortex: anterior cingulate (ACA), prelimbic (PL) and infralimbic (ILA) cortex, piriform cortex (PIR), associational visceral (VISC), gustatory (GU), agranular insular (AIp) cortical areas, retrosplenial (RSP), motor (MO), somatosensory (SS), auditory (AUD), visual (VIS), temporal associational (Tea), perirhinal (PERI) and entorhinal (ENT), and ectorhinal (ECT) cortical areas;
Basal ganglia: the nucleus accumbens (ACB), lateral septum (LS), the anterior part of the bed nuclei of the stria terminalis (BSTa), cortical amygdala and central amygdala (CEA);
Midline thalamus: paraventricular nucleus (PVT), intermediodorsal nucleus (IMB), central medial nucleus (CM), and rhomboid nucleus (RH);
Midbrain: geniculate complex (MG) and the periaqueductal gray (PAG);
Brainstem: locus coeruleus (LC).

Figure 3:
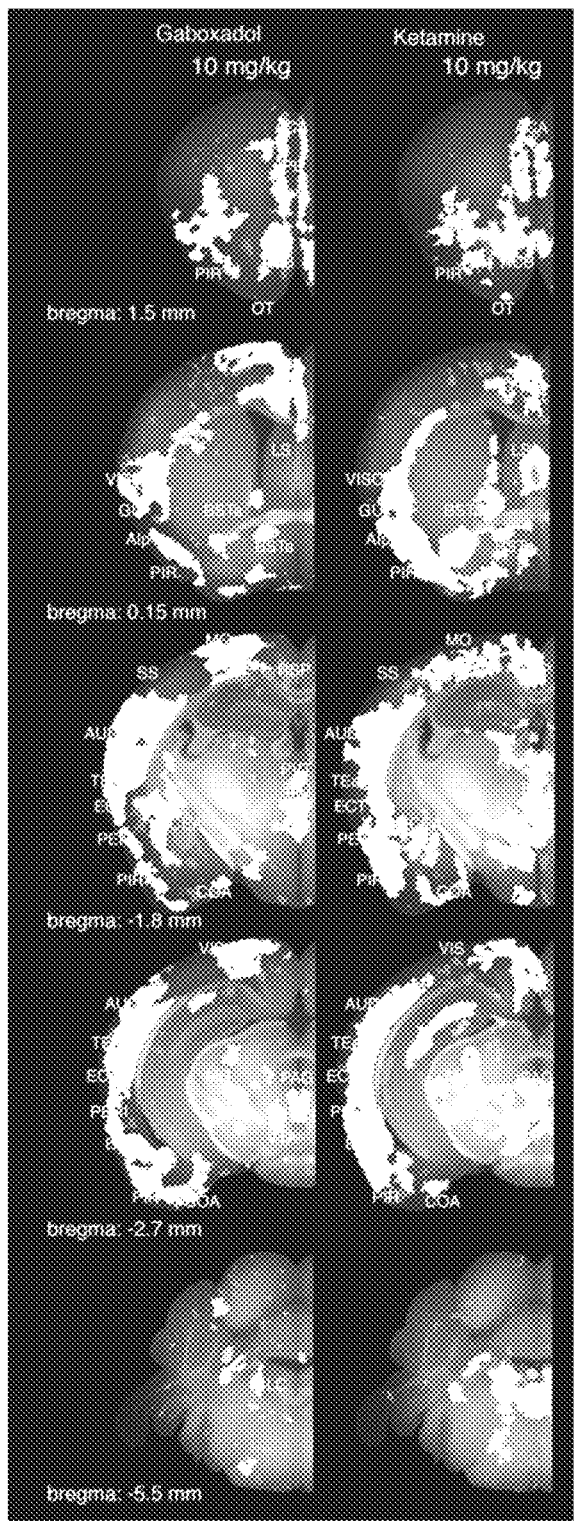

FIG. 3 shows an exemplary side-by-side comparison between a gaboxadol and a ketamine pharmacomap.

White color indicates the spatial areas of significant drug-evoked activation (green is for inhibition which in this case is only very sparse without clear anatomical significance). Gaboxadol at 10 mg/kg (left panels) evokes a broad brain activation that is highly similar to that of ketamine at 10 mg/kg (right panels). This includes:
Cortex: anterior cingulate (ACA), prelimbic (PL) and infralimbic (ILA) cortex, piriform cortex (PIR), associational visceral (VISC), gustatory (GU), agranular insular (AIp) cortical areas, retrosplenial (RSP), motor (MO), somatosensory (SS), auditory (AUD), visual (VIS), temporal associational (TEa), perirhinal (PERI) and entorhinal (ENT), and ectorhinal (ECT) cortical areas;
Basal ganglia: the nucleus accumbens (ACB), the anterior part of the bed nuclei of the stria terminalis (BSTa), cortical amygdala and central amygdala (CEA);
Midline thalamus: paraventricular nucleus (PVT), intermediodorsal nucleus (IMB), central medial nucleus (CM), and rhomboid nucleus (RH);
Midbrain: geniculate complex (MG) and the periaqueductal gray (PAG);
Brainstein: locus coeruleus (LC).

Figure 4:
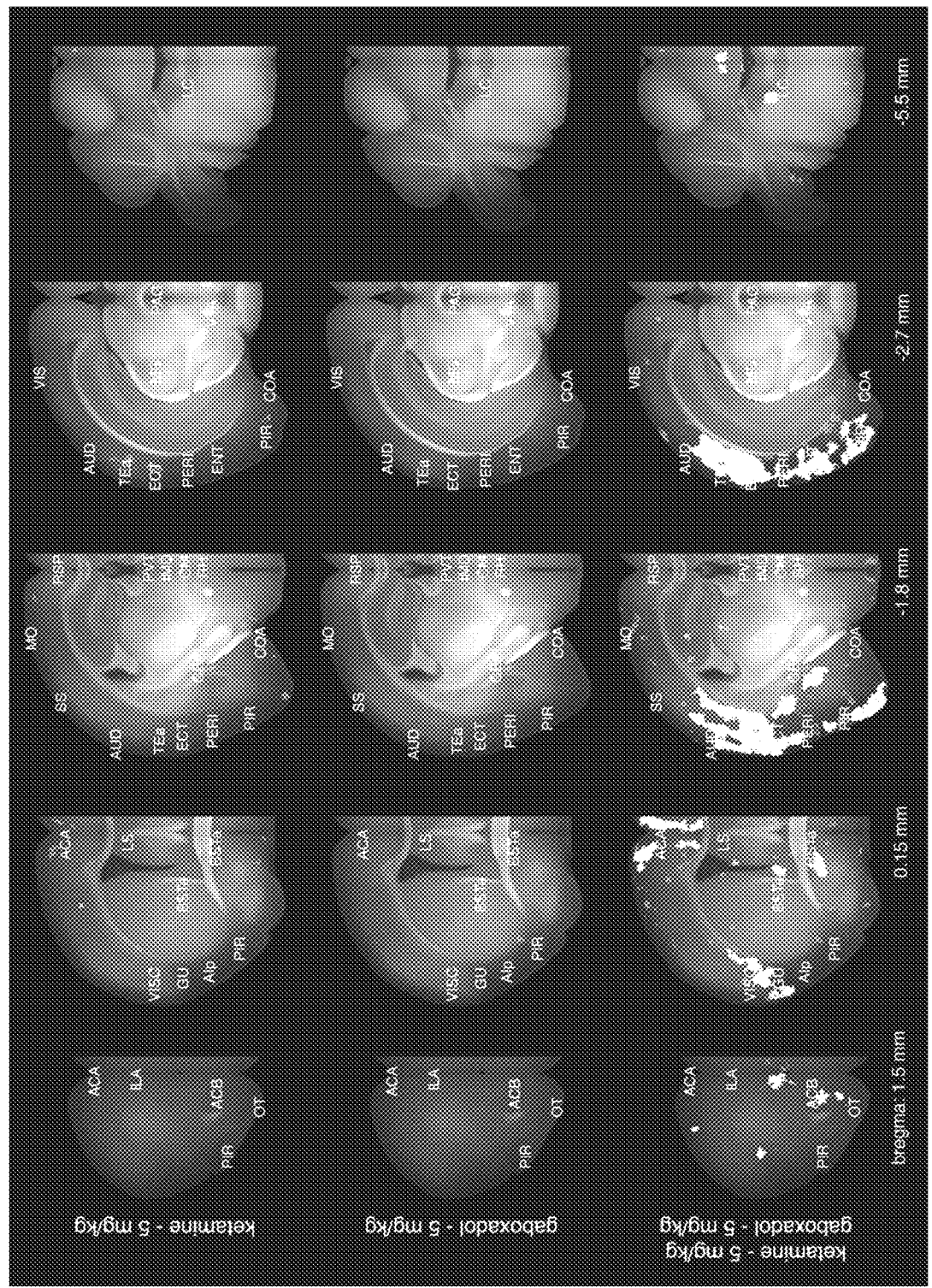

FIG. 4 shows an example of the synergistic effect obtained by the co-administration of gaboxadol and ketamine.

White color indicates the spatial areas of significant drug-evoked activation (green is for inhibition which in this case is only very sparse without clear anatomical significance). Gaboxadol at 3 mg/kg (left panel); Ketamine at 6 mg/kg (middle panel); Gaboxadol at 3 mg/kg and Ketamine at 6 mg/kg (right panel).

This includes:
Cortex: anterior cingulate (ACA), prelimbic (PL) and infralimbic (ILA) cortex, piriform cortex (PIR), associational visceral (VISC), gustatory (GU), agranular insular (AIp) cortical areas, retrosplenial (RSP), motor (MO), somatosensory (SS), auditory (AUD), visual (VIS), temporal associational (TEa), perirhinal (PERI) and entorhinal (ENT), and ectorhinal (ECT) cortical areas;
Basal ganglia: the nucleus accumbens (ACB), the anterior part of the bed nuclei of the stria terminalis (BSTa), cortical amygdala and central amygdala (CEA);
Midline thalamus: paraventricular nucleus (PVT), intermediodorsal nucleus (IMB), central medial nucleus (CM), and rhomboid nucleus (RH);
Midbrain: geniculate complex (MG) and the periaqueductal gray (PAG);
Brainstem: locus coeruleus (LC).

Figure 5:
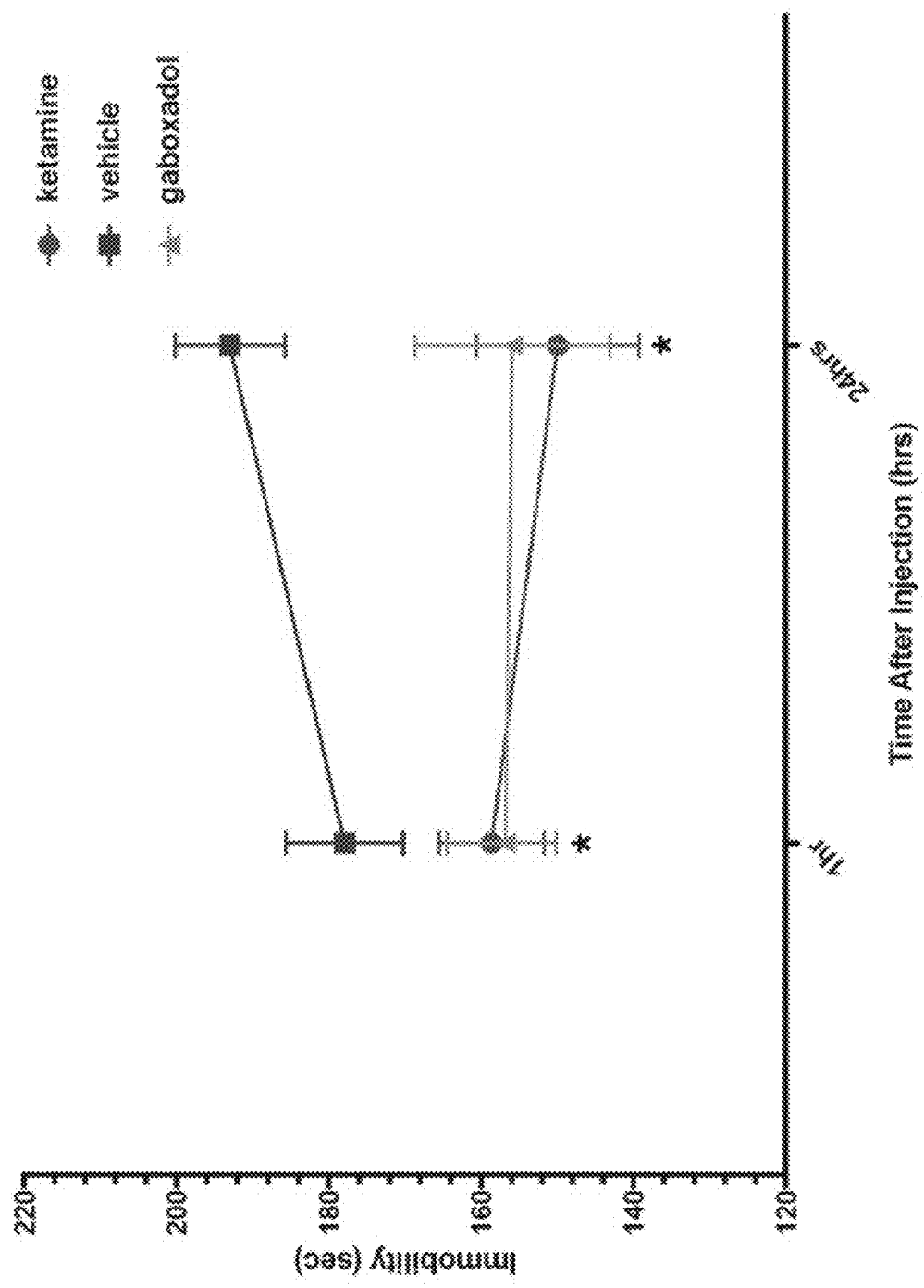

FIG. 5 shows exemplary results of a forced swim test. Both ketamine (round symbols) and gaboxadol (triangle symbols) significantly reduced the time spent in floating (immobility) during a 6 min forced swim compared to a control vehicle-treated group.

Figure 6:
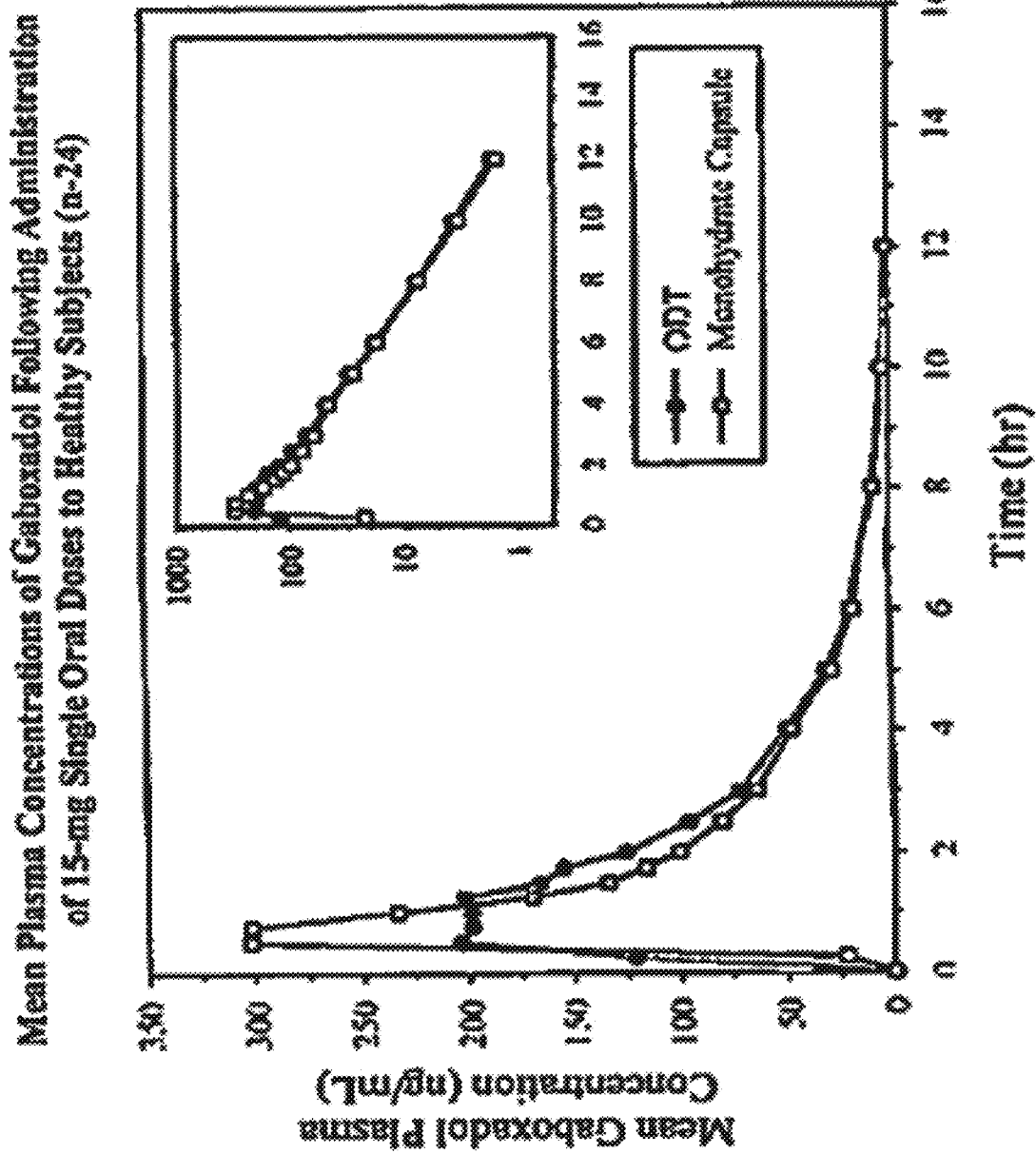

FIG. 6 shows exemplary mean plasma concentrations of gaboxadol following administration of 15-mg single oral doses to healthy subjects (n=24).

DETAILED DESCRIPTION OF THE PREFERRED EMBODIMENTS

The preferred embodiments of the present disclosure will now be described with reference to the drawings. Identical elements in the various figures are identified with the same reference numerals.

Reference will now be made in detail to each embodiment of the present disclosure. Such embodiments are provided by way of explanation of the present disclosure, which is not intended to be limited thereto. In fact, those of ordinary skill in the art may appreciate upon reading the present specification and viewing the present drawings that various modifications and variations can be made thereto.

Definitions

Unless defined otherwise, all technical and scientific terms used herein have the same meanings as commonly understood by one of skill in the art to which the disclosure herein belongs.

As used herein, the singular forms "a," "an," and "the," are intended to include the plural forms as well, unless the context clearly indicates otherwise.

The phrase "and/or," as used herein in the specification and in the claims, should be understood to mean "either or both" of the elements so conjoined, i.e., elements that are conjunctively present in some cases and disjunctively present in other cases. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In certain embodiments, the term "about" or "approximately" as used herein means within an acceptable error range for the particular value as determined by one of ordinary skill in the art, which will depend in part on how the value is measured or determined, i.e., the limitations of the measurement system.

In certain embodiments, "about" can mean within 3 or more than 3 standard deviations, per the practice in the art.

In certain embodiments, particularly with respect to biological systems or processes, the term can mean within an order of magnitude, preferably within 5-fold, and more preferably within 2-fold, of a value.

In certain embodiments, when the term "about" or "approximately" is used in conjunction with a numerical range, it modifies that range by extending the boundaries above and below those numerical values. In general, the term "about" is used herein to modify a numerical value above and below the stated value by a variance of 20%, 10%, 5?, or 1%. In certain embodiments, the term "about" is used to modify a numerical value above and below the stated value by a variance of 10%. In certain embodiments, the term "about" is used to modify a numerical value above and below the stated value by a variance of 5%. In certain embodiments, the term "about" is used to modify a numerical value above and below the stated value by a variance of 1%.

When a range of values is listed herein, it is intended to encompass each value and sub-range within that range. For example, "1-5 ng" or "from about 1 ng to about 5 ng" is intended to encompass 1 ng, 2 ng, 3 ng, 4 ng, 5 ng, 1-2 ng, 1-3 ng, 1-4 ng, 1-5 ng, 2-3 ng, 2-4 ng, 2-5 ng, 3-4 ng, 3-5 ng, and 4-5 ng.

It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

"Suicidal ideation", also described as "suicidalness", "suicidal thoughts", "suicidal impulse", "suicidal compulsions", "suicidalism", and "suicidality", is a recognized condition wherein the patient examination indicates a subjective wish to die, passive and active suicide attempt thoughts, significant duration and frequency of ideation, lack of control, lack of deterrents, preparatory behavior for an attempt, and other symptoms. It may be assessed by score on the Scale for Suicidal Ideation (Beck et al. J Consult Clin Psychol 1979; 47:343-352). Suicidal ideation includes thinking about or having an unusual preoccupation with suicide. The range of suicidal ideation varies greatly from fleeting thoughts, to extensive thoughts, to detailed planning, role playing (e.g., standing on a chair with a noose), and incomplete attempts. Suicidal ideation is distinct from, and possibly overlapping with conditions which are diagnosed (under DSM-V) as major depressive disorder, treatment resistant depression, disruptive mood dysregulation disorder, major depressive disorder (including major depressive episode), persistent depressive disorder (dysthymia), premenstrual dysphoric disorder, substance/medication-induced depressive disorder, depressive disorder due to another medical condition, other specified depressive disorders, and unspecified depressive disorder.

A patient "at risk of suicide" means a human subject having a clinically or subjectively assessed short- or medium-term risk of taking active steps towards self-harm with a risk of death. Patients at risk of suicide include patients diagnosed under DSM-V or other criteria as experiencing suicidal ideation, acute suicidality, recurrent thoughts of death and/or suicidal attempts. The term "at risk of suicide" does not necessarily follow from a diagnosis of depression, major depressive disorder, treatment resistant depression, bi-polar disorder, mania and other disturbed psycho-social conditions but distinct sub-sets of such patients may be separately identified as being at risk of suicide.

In certain embodiments, a person at risk of suicide has not been diagnosed with any psychiatric illness including major depression.

In certain embodiments, a person at risk of suicide does not have major depression.

In certain embodiments, a person at risk of suicide does not have Huntington's disease, Parkinson's disease, Amyotrophic Lateral Sclerosis, Alzheimer's disease, Fragile X syndrome, or Angelman syndrome.

In certain embodiments, a person at risk of suicide is being treated with antidepressants.

"A method of reducing risk of suicide" means, in a patient at risk of suicide, a medical or psychosocial intervention intended to reduce such risk, which intervention is established as effective on the basis of a clinical study in a population of patients at risk of suicide. Similarly, an intervention "sufficient to reduce the risk of suicide and/or self-harm" means an intervention that has been tested in a population of patients at risk of suicide and/or self-harm, or any complex animal model comparable to such condition, and found statistically across the population to reduce incidents of suicide, self-harm or animal behaviours correlated with such conditions.

"Effective amount" or "therapeutically effective amount" means a dosage sufficient to alleviate one or more symptoms of the condition being treated, or to otherwise provide a desired pharmacological and/or physiologic effect, as may be determined by an objective measure or a patient derived subjective measure.

In certain embodiments, an "effective amount" or "therapeutically effective amount" of gaboxadol means the amount of a single dose of gaboxadol sufficient to relieve suicidal ideation within 12, 24, 36, 48 hours or 60 hours.

In certain embodiments, an "effective amount" or "therapeutically effective amount" of gaboxadol means the amount of two consecutive doses of gaboxadol sufficient to relieve suicidal ideation within 12, 24, 36, 48 hours or 60 hours.

The term "Improvement" refers to the reduction of risk of suicide measured relative to at least one symptom.

"Improvement in next day functioning" or "wherein there is improvement in next day functioning" refers to improvement wherein the beneficial effect of at least one symptom lasts over a period of time, e.g., 6 hours, 12 hours, 24 hours etc.

"for oral administration" refers to a dosage form which may be conveniently administered orally to a human subject.

"for intranasal administration" refers to a dosage form which may be conveniently administered intranasally to a human subject.

"Patient in need thereof" includes individuals that have been diagnosed at risk of suicide or have symptoms of risk of suicide.

"Pharmaceutically acceptable" refers to molecular entities and compositions that are "generally regarded as safe"—e.g., that are physiologically tolerable and do not typically produce an allergic or similar untoward reaction, such as gastric upset and the like, when administered to a human. In certain embodiments, this term refers to molecular entities and compositions approved by a regulatory agency of the federal or a State government, e.g., the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

"Pharmacokinetics" (PK) parameters are used to describe the rate of absorption of a substance into a biological system. Graphing a substance's serum concentration versus time reveals of the drug's basic PK properties: the maximum concentration the drug attains ($C_{max}$), the time at which this maximum concentration occurs (Tmax), and the area under the concentration-versus-time curve (AUC) which estimates total systemic exposure. $AUC_{0-\infty}$ is the total area under the plasma drug concentration-time curve, from drug administration until the drug is eliminated (ng*hr/ml). The area under the curve is governed by clearance. Clearance is defined as the volume of blood or plasma that is totally cleared of its content of drug per unit time (ml/min). "Treating" or "treatment" refers to alleviating the clinical symptoms of a disease or condition in a subject that may be afflicted with the disease or condition. In certain embodiments, "treating" or "treatment" may refer to preventing the appearance of clinical symptoms of a disease or condition in a subject that may be afflicted with or predisposed to the disease or condition. The "treating" or "treatment" can also refer to arresting or reducing development of, or at least one clinical or subclinical symptom of, the disease or condition. "Treating" or "treatment" can refer to a statistically significant, mathematically significant reduction in a symptom of acute suicidality. In certain embodiments, "treating" or "treatment" can refer to the improvement of a symptom perceptible to the subject and/or the physician. Permanently curative treatment is not required to achieve "treatment" herein.

"Unit dosage form" or "UDF" means a physically fixed unit dose of a formulation which is conveniently administered in unit form (e.g. requires no measuring or adjusting of dosage before consumption). A patient may consume one or more UDFs at a time.

"Rapid antidepressant", "rapid-acting antidepressant" or "fast-acting antidepressant" refers to a medication capable of delivering therapeutic relief (as may be objectively or subjectively observed) within 24 hrs from first treatment, also referred to herein as rapid alleviation of depressive symptoms.

"Rapid anti-suicidal agent", "rapid-acting anti-suicidal agent" or "fast-acting anti-suicidal agent" refers to a medication capable of delivering therapeutic relief from suicidal ideation (as may be objectively or subjectively observed) within 24 hrs from first treatment, also referred to herein as rapid alleviation of suicidality.

The present disclosure is supported by the inventors' discovery, using a novel brain imaging technique, that the administration of a high dose gaboxadol, e.g. at least >50 mg human equivalent dose (HED) evokes a broad brain activation pattern which very similar to ketamine with some key differences related to a better safety profile of gaboxadol. As shown in the Examples below, the wide cortical activation and the midline thalamic activation as well as activation of midbrain periaqueductal grey (PAG) and brainstem locus coeruleus (LC) is very similar between gaboxadol and ketamine. In addition, the brain imaging also shows a synergistic effect between gaboxadol and ketamine, suggesting that even though the drugs act at very different molecular targets, their downstream effect leads to a shared brain circuit-based mechanisms. By analogy to ketamine, which has clearly identified therapeutic potential for providing a fast-acting relief of depression and treating suicidal ideation, the present disclosure identifies for the first time an unexpected therapeutic utility of high dose gaboxadol, e.g., at >50 mg HED, as a fast-acting antidepressant and anti-suicidal agent. What is more, gaboxadol may provide significant patient advantages over ketamine because gaboxadol is not known to induce the substantial dissociative side-effects known to result from ketamine administration.

The invention establishes for the first time that gaboxadol is an excellent agent for rapidly reducing risk of suicide in patients experiencing suicidal ideation, acute suicidality, risk of self-harm and/or for rapid onset treatment in depression.

Existing Treatments and Ketamine Clinical Trials for Reducing Risk of Suicide

Current treatment options for patients at risk of suicide are limited by the slow time course of change in suicidal thoughts. For instance, in major depressive disorder (MDD) patients receiving thrice-weekly electroconvulsive therapy, suicidal thoughts persisted in 62% of patients after 1 week of treatment and 39% after 2 weeks. Conventional antidepressant treatment produced slower and less robust response in elderly MDD patients with moderate-to-high suicide risk than in non-suicidal patients. Standard antidepressants may reduce suicidal ideation and behavior in depressed adults, mediated by improvement in depressive symptoms, but this effect takes weeks. Other somatic treatments with some evidence for anti-suicidal effects include clozapine in schizophrenia and ECT in mood disorders.

Suicidal depressed patients need rapid relief of suicidal ideation. Depression remits in one-third or fewer patients, and fewer than half achieve even 50% relief with typical first line medications. Although suicidal behavior is usually associated with depression, most antidepressant trials have excluded suicidal patients and did not assess suicidal ideation and behavior systematically, which has resulted in limited data on this topic. Depression predicts suicide attempts via its effect on suicidal ideation.

Ketamine, a drug with dissociative and glutamate NMDA receptor-blocking properties that was approved by the U.S. Food and Drug Administration in 1970 for anesthetic use, has recently become a target of research for its antidepressant effects, which occur within hours at subanesthetic doses. Reports of reduction in suicidal ideation after ketamine infusion are promising, but the conclusiveness of results for major depression has been limited by measurement of suicidal ideation with a single item from a depression inventory, lack of a control group, use of a saline control, and use of samples with low levels of suicidal ideation or mixed diagnoses.

Clinical trials are underway to establish the efficacy of ketamine on reduction of suicidal ideation. An example is may be found at ClinicalTrials.gov Identifier: NCT01700829, described in associated publication (Am J Psychiatry 175:4, April 2018). This trial is a randomized clinical trial of an adjunctive IV infusion of ketamine compared with the short-acting benzodiazepine anesthetic midazolam in patients with major depressive disorder who had clinically significant suicidal ideation, as assessed by score on the Scale for Suicidal Ideation (SSI). The primary outcome measure was SSI score 24 hours after infusion. Other outcome measures include global depression ratings, clinical ratings during 6-week open follow-up treatment, and safety measures. IV ketamine has been effective in treating acute cases of suicidality et al. (2015) Innov Clin Neurosci. 2015 January-February; 12(1-2): 29-31.) Janssen Pharmaceuticals is also conducting ketamine clinical trials with ketamine on MDD, some details of which may be found at ClinicalTrials.gov Identifier: NCT01627782.

Gaboxadol and Pharmaceutically Acceptable Salts Thereof

Described herein are methods and compositions for reducing risk of suicide with gaboxadol or a pharmaceutically acceptable salt thereof.

The invention employs a first treatment of gaboxadol with no further administration of gaboxadol or a pharmaceutically acceptable salt thereof in the 3 or more days following the first treatment.

In certain embodiments, gaboxadol is administered once with no additional treatment for 1, 2, 3, 4, 5, 6, 7, 8, 9 or 10 days.

This invention provides a striking contrast with previous proposed treatment modalities using lower doses (e.g., <40 mg single dose) of gaboxadol. Previous suggested uses, none of which have been clinically approved, include as an analgesic, an anxiolytic, combined anxiolytic and anti-depressant acting as an add-on to escitalopram, for treatment of insomnia and for treatment of symptoms of certain genetic developmental disorders. By contrast the invention provides utility of gaboxadal at high doses (e.g., >50 mg per single dose) for reducing risk of suicide in an urgent care situation and rapid relief of depression, for example treatment-resistant depression and/or at the onset of a treatment of major depression to bridge the delayed effect of traditional antidepressants.

In certain embodiments, the incidence of suicidal ideation within a population of patients suffering from acute suicidality is reduced by 10%, 20%, 30%, 40%, 50?, 60%, 70%, 80%, 90%, 95% or 100% within 24 hours after administration of the first treatment.

Further, the invention provides a previously unrecognized "first treatment" approach to dosing of gaboxadol. Previously when gaboxadol was proposed as an analgesic or anxiolytic agent, it was presumed to require frequent maintenance dosing. This was especially the case because gaboxadol is a selective GABAA receptor agonist with a relatively short half-life ($t_{1/2}=1.5$ h). By contrast, our invention provides a first treatment of high dose (>50 mg) of gaboxadol leading to rapid onset and durable effect of treatment for at least 3 days after administration.

In certain embodiments, the first treatment dose of gaboxadol leads to a rapid onset and durable effect of treatment for at least 3, 4, 5, 6, or 7 days after administration.

Disclosed herein are methods of reducing risk of suicide by administering to a patient in need thereof a first treatment of gaboxadol or a pharmaceutically acceptable salt thereof. In certain embodiments, methods include administering to a patient in need thereof a first treatment of about 50 mg to about 300 mg gaboxadol or a pharmaceutically acceptable salt thereof wherein the first treatment provides improvement in the patient for 3, 4, 5, 6, or 7 or more days after administration to the patient. No gaboxadol in any form is administered to the patient for 3, 4, 5, 6, or 7 or more days following the first treatment.

Embodiments described herein provide that a patient in need thereof is administered a pharmaceutical composition including gaboxadol or a pharmaceutically acceptable salt thereof. Gaboxadol or pharmaceutically acceptable salt thereof may be provided as an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylene-salicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic or theophylline acetic acid addition salts, as well as the 8-halotheophyllines, for example 8-bromo-theophylline. In other suitable embodiments, inorganic acid addition salts, including but not limited to, hydrochloric, hydrobromic, sulfuric, sulfamic, phosphoric or nitric acid addition salts may be used.

In certain embodiments, gaboxadol is provided as gaboxadol monohydrate. One skilled in the art will readily understand that the amounts of active ingredient in a pharmaceutical composition will depend on the form of gaboxadol provided. For example, pharmaceutical compositions of including 5.0, 10.0, 15.0, 33.0, 50.0 or 150.0 mg gaboxadol correspond to 5.6, 11.3, 16.9, 37.0, 56 or 169 mg gaboxadol monohydrate, respectively.

In certain embodiments, gaboxadol is crystalline, such as the crystalline hydrochloric acid salt, the crystalline hydrobromic acid salt, or the crystalline zwitter ion monohydrate. In certain embodiments, gaboxadol is provided as a crystalline monohydrate.

Deuteration and/or fluorination of pharmaceuticals to improve pharmacokinetics (PK), pharmacodynamics (PD), and toxicity profiles, has been demonstrated previously with some classes of drugs. Accordingly, the use of deuterium or fluorine enriched gaboxadol is contemplated and within the scope of the methods and compositions described herein. Deuterium or fluorine can be incorporated in any position in replacement of hydrogen synthetically, according to the synthetic procedures known in the art. For example, deuterium or fluorine may be incorporated to various positions having an exchangeable proton, such as the amine N—H, via proton-deuterium equilibrium exchange. Thus, deuterium or fluorine may be incorporated selectively or non-selectively through methods known in the art to provide deuterium enriched gaboxadol. See, for example, Journal of Labeled Compounds and Radiopharmaceuticals 19(5) 689-702 (1982).

Deuterium or fluorine enriched gaboxadol may be described by the percentage of incorporation of deuterium or fluorine at a given position in the molecule in the place of hydrogen. For example, deuterium enrichment of 1% at a given position means that 1% of molecules in a given sample contain deuterium at that specified position. The deuterium enrichment can be determined using conventional analytical methods, such as mass spectrometry and nuclear magnetic resonance spectroscopy. In certain embodiments deuterium enriched gaboxadol means that the specified position is enriched with deuterium above the naturally occurring distribution {i.e., above about.0156%). In certain embodiments deuterium enrichment is no less than about 1%, no less than about 5%, no less than about 10%, no less than about 20%, no less than about 50%, no less than about 70%, no less than about 80%, no less than about 90%, or no less than about 98% of deuterium at a specified position.

Exemplary Dosages of Gaboxabol

In certain embodiments methods of reducing risk of suicide include administering to a patient in need thereof a first treatment of a pharmaceutical composition including about 1 mg to about 1000 mg gaboxadol or a pharmaceutically acceptable salt thereof.

In certain embodiments, the pharmaceutical compositions include 1 mg to 150 mg, about 5 mg to about 20 mg, about 33 mg to about 75 mg, about 33 mg to about 100 mg, or about 33 mg to about 150 mggaboxadol or a pharmaceutically acceptable salt thereof. In certain embodiments, the pharmaceutical compositions include about 1, 5, 10, 15, 20, 25, 30, 33, 35, 40, 45, 50, 55, 60, 65, 70, 75, 80, 85, 90, 95, 100, 105, 110, 115, 120, 125, 130, 135, 140, 145, 150, 175, 200, 250, 500 or 1000 mg gaboxadol or a pharmaceutically acceptable salt thereof.

In a preferred embodiment, when gaboxadol is used as a single or primary agent, the first treatment is a single dose of about 33 mg to about 1000 mg.

In certain embodiments, when gaboxadol is used as a single or primary agent, the first treatment is a single dose of about 50 mg to about 300 mg.

In certain embodiments, when gaboxadol is used as a single or primary agent, the first treatment is a single dose of about 33 mg to about 150 mg.

In certain embodiments, when gaboxadol is used as a single or primary agent, the first treatment is a single dose of about 40 mg to about 150 mg.

In certain embodiments, when gaboxadol is used as a single or primary agent, the first treatment is a single dose of about 50 mg to about 150 mg.

In certain embodiments, when gaboxadol is used as a single or primary agent, the first treatment is a single dose of about 60 mg to about 300 mg.

In certain embodiments, when gaboxadol is used as a single or primary agent, the first treatment is a single dose of about 70 mg to about 300 mg.

In certain embodiments, when gaboxadol is used as a single or primary agent, the first treatment is a single dose of about 80 mg to about 300 mg.

In certain embodiments, when gaboxadol is used as a single or primary agent, the first treatment is a single dose of about 90 mg to about 300 mg.

In certain embodiments, when gaboxadol is used as a single or primary agent, the first treatment is a single dose of about 100 mg to about 300 mg.

In certain embodiments, when gaboxadol is used as a single or primary agent, the first treatment is a single dose of about 110 mg to about 300 mg.

In certain embodiments, when gaboxadol is used as a single or primary agent, the first treatment is a single dose of about 120 mg to about 300 mg.

In certain embodiments, when gaboxadol is used as a single or primary agent, the first treatment is a single dose of about 130 mg to about 300 mg.

In certain embodiments, when gaboxadol is used as a single or primary agent, the first treatment is a single dose of about 140 mg to about 300 mg.

In certain embodiments, when gaboxadol is used as a single or primary agent, the first treatment is a single dose of about 150 mg to about 300 mg.

In certain embodiments, when gaboxadol is used as a single or primary agent, the first treatment is a single dose of about 200 mg to about 300 mg.

In certain embodiments, when gaboxadol is used as a single or primary agent, the first treatment is a single dose of about 250 mg to about 300 mg.

In a preferred embodiment, when the gaboxadol first treatment is in combination with another agent such as ketamine, it may be used at a lower dose of about 5 mg to about 50 mg (herein sometimes referred to as a "synergistic dose" or a "low dose").

Pharmaceutical compositions herein may be provided with immediate release or standard release profiles. Compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, disintegrants, fillers, and coating compositions. Those skilled in the art are familiar with identifying preferred formulation techniques for a unit dosage form (UDF). In a preferred embodiment, the UDF is a pill, tablet, capsule, film, or wafer, any of which may optionally be orally disintegrating, or a lollipop, lozenge, oil, tincture, or syrup. The formulation process will be adjusted accordingly. Pills and tablets are prepared from solid formulations. Syrups, oils and tincture are liquid formulations. An orally disintegrating film, wafer, tablet or a lollipop or lozenge provides the UDF in an oral form wherein the active ingredients are at least partly absorbed directly in the buccal cavity. Capsules may be either solid formulations (e.g. powders or particles in a hard-gel) or liquid formulations (e.g. oil-based formulations used in soft-gels). Oil based formulations with little or no water are typically easily encapsulated. Oil-in-water formulations may comprise microemulsions, liposomes, nanoemulsions and other forms known in the art.

A wide variety of technologies are available for a buccal or sublingual formulation such as an orally disintegrating thin film, wafer or tablet, or a lollipop, and/or lozenge. Sublingual tablets, wafers, films and strips can be designed to rapidly disintegrate (5-15 seconds) providing rapid access to buccal cavity capillaries and avoid the hostile environment of the gastrointestinal track. Lollipops and lozenges provide a combination of buccal and gastric administration. The technologies are widely used with therapeutic agents where rapid onset is desired. (See Lamey and Lewis "Buccal and Sublingual Delivery of Drugs" Ch 2 in "Routes of Drug Administration" Ed. Florence and Salole (Butterworth-Heinemann)). Example 6 below provides an example of an ODT.

Further formulations of gaboxadol, or pharmaceutically acceptable salts thereof, are disclosed in the following patent publications: WO 2018144827, US 20110082171, US 20090048288, WO 2006118897, WO 2006102093, GB 2410434, US 20050137222, WO 2002094225 WO 2001022941, the contents of which are incorporated by reference herein in their entireties.

First Treatment and its Therapeutic Effect

The invention contemplates a first treatment with gaboxadol, or pharmaceutically acceptable salt thereof, upon diagnosis of a patient as being at risk of suicide. Typically, patients present at an urgent care facility or at a doctor's office where the diagnosis is made. The method of the invention contemplates administration of the first treatment with patient consent promptly after the diagnosis.

The invention also contemplates a first treatment with gaboxadol, or pharmaceutically acceptable salt thereof, upon first diagnosis of a depression in a patient not treated with antidepressants and in need of rapid antidepressive relief before the delayed onset of clinically efficacy of traditional antidepressants, such as selective serotonin reuptake inhibitors (SSRIs), serotonin and noradrenaline reuptake inhibitors (SNRIs), tricyclic antidepressants (TCAs), tetracyclic antidepressants (TeCAs), monoamine oxidase inhibitors (MAOIs), or noradrenaline and specific serotoninergic antidepressants (NASSAs). Typically, patients present at an urgent care facility or at a doctor's office where the diagnosis is made. The method of the invention contemplates administration of the first treatment with patient consent promptly after the diagnosis.

The invention also contemplates a treatment with gaboxadol, or pharmaceutically acceptable salt thereof, in a patient with treatment-resistant depression and in need of rapid anti-depressive relief when treatment with traditional antidepressants when such treatment either fails to induce a clinical relief or fails to provide a continuous relief after an initial period of successful treatment. Typically, patients present at an urgent care facility or at a doctor's office where the diagnosis is made. The method of the invention contemplates administration of the first treatment with patient consent promptly after the diagnosis. In certain embodiments, the patient has received electric shock therapy.

In certain embodiments, the first treatment comprises a dose of from 50 mg to 300 mg of gaboxadol, or pharmaceutically acceptable salt thereof. In certain embodiments, the first treatment comprises a dose of from about 50 mg, to 150 mg, about 50 mg to about 75 mg, about 50 mg to about 100 mg, about 50 mg to about 150 mg, about 50 mg to about 200 mg, about 50 mg to about 250 mg, or about 50 mg to about 300 mg, of gaboxadol or a pharmaceutically acceptable salt thereof. Preferably the dose form is rapidly absorbed by the patient and provides rapid onset for reduction in the symptoms of suicidal ideation.

A preferred biomarker measure of rapid onset is to measure brain activity by electroencephalography (EEG). EEG is a measure of neurological activity well known to those skilled in the art. Standard techniques and instruments are widely available. Low frequency wavelength emissions are measured across a spectral range typically 0.2-35 Hz at multiple sites on the patient's head. Power spectra are assessed at each wavelength (or across a range of wavelengths) to observe and detect neurological activity. EEG may be used in the context of measuring neurological response to drugs such as gaboxadol as described in Dijk et al, (2010) J. Psychopharmacology. 24(11) 1613-1618. See also Lundahl et al. (2011) J Psychopharmacol 26: 1081.

Magnetoencephalography is an alternative neuroimaging technique with high temporal resolution and moderately good spatial resolution that allows direct measurement of the magnetic fields generated by synchronized ionic neural currents in the brain. When combined with pharmacological interventions, MEG (pharmaco-MEG) is a powerful tool for measuring the effects of experimental modulations of neurotransmission in the living human brain, in both patient and healthy control groups (Muthukumaraswamy, 2014). Compared with EEG, it can provide superior spatial resolution, and reduced contamination of the brain signals by physiological artefacts such as blinks and muscle potentials. See Nutt et al. Neuropharmacology 88 (2015) 155-163.

The invention contemplates that the first treatment of gaboxadol, or pharmaceutically acceptable salts thereof, demonstrates rapid onset and induces rapid reduction of symptoms of suicidal ideation. An biomarker measure of the rapid onset may be obtained by EEG. An EEG power density increase of about 30% or more across spectra in the 0.25Hz-8.0Hz range within 180 minutes of the first treatment is indicative of rapid onset of effect. Preferably patients will record a power density increase of about 50% or more across this range. More preferably patients will record a power density increase of about 50% or more across the 4.75-8.0 Hz range. EEG power density increases have been described in Dijk (2010) and Lundahl (2011), upon administration of gaboxadol, in the context of other disease indications.

Alternatively, MEG may be employed as a biomarker to observe rapid onset of therapeutic effect of the first treatment. In the context of a different therapeutic indication, Nutt et al (2015) observed the administration of gaboxadol to lead to a whole head MEG planar gradiometer increase of +3 or higher in the combined delta, theta and alpha activity at the time point 160 minutes after the first treatment. The method of the present invention anticipates an increase of +3 or greater within 180 minutes of the first treatment.

As used herein, "rapid onset" means that one or more objectively observable symptoms of the condition being treated (e.g. risk of suicide, suicidal ideation, depression, treatment resistant depression, as described herein) is alleviated or reduced within 24 hours of the first treatment, and preferably within 6 hours of first treatment.

The method of the invention anticipates a durable effect, meaning that the first treatment of gaboxadol reduces the symptoms of suicidal ideation for about 3, 4, 5, 6, 7, 8, 9, 10 or more days post-administration.

Without wishing to be bound by theory, it is contemplated based on the examples below, that the first treatment induces a chemical form of brain activation through δ subunit-containing GABAA receptors which may be interpreted as a physiological effect comparable to electroconvulsive therapy (ECT). The effect of the first treatment is not enhanced by maintenance dosing of gaboxadol in the first 3 days after the first treatment. In fact, no further dosing is required until the patient symptoms indicate a further treatment would be beneficial, which may arise 3, 4, 5, 6 or more days following said first treatment, or may not arise at all for a longer period. Stated otherwise, additional treatment with gaboxadol is to be specifically avoided in the 3-day period following completion of the first treatment as this will reduce the effectiveness of treatment. The 3-day or longer period following the first treatment may be considered a wash-out period. The 3-day no-treatment period may be extended to 4, 5, or 6 days, or longer, if reduced symptoms of suicidal ideation persist. It is further understood that if or when suicidal ideation returns at a time greater than 3 days after the first treatment, a follow-up treatment of gaboxadol or pharmaceutically acceptable salt thereof may be administered. Such follow-up treatment would be considered a "first treatment" as disclosed herein. In some cases, 4-day, 5-day, 6-day or weekly dosing, each of which may be called "intermittent dosing" of gaboxadol, will be indicated for a patient. In each case the dosing is considered a "first treatment" according to the present invention.

In a further embodiment, the "first treatment" of gaboxadol, or pharmaceutically acceptable salt thereof, comprises an initial administration of gaboxadol, or pharmaceutically acceptable salt thereof, and optionally, a second administration of gaboxadol, or pharmaceutically acceptable salt thereof, within 12 hours immediately folio rig the initial administration. In certain embodiments, the total amount of the first and second administration does not exceed 300 mg of gaboxadol, or pharmaceutically acceptable salt thereof.

The decision regarding the optional second administration is based on measuring indicators of the patient's response to the first administration. Any response of the patient may be used to make the decision, including a change in any behaviour or any physiological or biological marker of response. An insufficient response to the first administration will be suggestive of the recommendation for a second administration as part of the first treatment.

A preferred patient response for determining sufficiency of response will be based on measuring the patient's neurological response according to EEG or MFG. An "insufficient response" includes an EEG power density increase of less than 50% or optionally less than 30% across the spectra 0.25-8.0 Hz at the time point 160 minutes after the first administration. An "insufficient response" also includes an EEG power density increase of less than 50% or optionally less than 30% across the spectra 4.75-8.0 Hz at the time point 160 minutes after the first administration An insufficient response to the first administration also includes a whole head MEG planar gradiometer increase of less +3 in the combined delta, theta and alpha activity at the time point 160 minutes after the first administration.

An insufficient response also includes a continuance of observable symptoms of suicidal ideation, acute suicidality, risk of self-harm and/or treatment resistant depression.

A second administration of gaboxadol or past (as part of the "first treatment") will be administered within a maximum of 12 hours from the first administration (of the first treatment) in order to reduce the risk of suicide. Preferably the second administration will follow shortly after the confirmation of insufficient response by EEG or MEG at the 160 min time point. The second administration may be delayed for various patient care reasons but to achieve the desirable effect of the invention should be administered within 12 hours of the first administration.

The wash-out period between the first treatment and any subsequent treatment(at least 3 days after the first treatment) reflects the neurological impact of the gaboxadol treatment which corresponds to the observation in ketamine clinical trials of an extended period of 7 or more days where a first treatment is sufficient to alleviate suicidal ideation, recurrent thoughts of death, actions towards suicide and suicide attempts as described in U.S. Pat. No. 9,359,220, the content of which is incorporated by reference herein in its entirety. It also corresponds to the observed period of reduction of suicidal ideation in certain patients who have undergone electroconvulsive therapy. Treatments in the intervening wash-out period, such as maintenance doses of therapeutic agent, or further electroconvulsive therapy are understood to be counter-effectual due to the re-stimulation of neurological areas which would interfere with the desirable pattern of neurological recovery from the electro- or chemical-shock of the first treatment.

Dose Form

The invention contemplates administration of gaboxadol, or pharmaceutically acceptable salt thereof, designed for rapid onset of treatment effect. A wide variety of dose forms may be employed including those described previously in the literature. Preferred dose forms are suitable for oral or intranasal administration.

Oral administration can employ any orally acceptable form including pills, tablets, capsules, syrup etc. Such forms can be manufactured according to techniques well known to those skilled in the art.

A particularly preferred form for rapid onset is an orally disintegrating dosage form (ODDF) which provides immediate release in the patient's buccal cavity enhancing buccal absorption of the drug. An ODDF is a solid dosage form containing a medicinal substance or active ingredient which disintegrates rapidly, usually within a matter of seconds when placed upon the tongue. The disintegration time for ODDFs generally range from one or two seconds to about a minute. ODDFs are designed to disintegrate or dissolve rapidly on contact with saliva. This mode of administration can be beneficial to people who may have problems swallowing tablets as is common with conditions which are psychiatric in nature.

In certain embodiments, pharmaceutical compositions herein provide immediate release of gaboxadol or a pharmaceutically acceptable salt thereof which when administered to an oral cavity, disintegrates in less than one minute, less than 55 seconds, less than 50 seconds, less than 45 seconds, less than 40 seconds, less than 35 seconds, less than 30 seconds, less than 25 seconds, less than 20 seconds, less than 15 seconds, less than 10 seconds, or less than 5 seconds based upon, e.g., the United States Pharmacopeia (USP) disintegration test method set forth at section 701, Revision Bulletin Official Aug. 1, 2008.

In preferred embodiments, the ODDF results in pharmacokinetic properties which include a Tmax of 20 minutes or less. In certain embodiments, pharmaceutical compositions herein provide of 20 minutes or less, a Tmax of 19 minutes or less, a Tmax of 18 minutes or less, a Tmax of 17 minutes or less, a Tmax of 16 minutes or less, a Tmax of 15 minutes or less, a Tmax of 14 minutes or less, a Tmax of 13 minutes or less, a Tmax of 12 minutes or less, a Tmax of 11 minutes or less, a Tmax of 10 minutes or less, a Tmax of 9 minutes or less, a Tmax of 8 minutes or less, a Tmax of 7 minutes or less, a Tmax of 6 minutes or less, or a Tmax of 5 minutes or less. Such pharmaceutical compositions include ODDFs such as orally disintegrating tablets (ODTs).

An ODT is a solid dosage form containing a medicinal substance or active ingredient which disintegrates rapidly, usually within a matter of seconds when placed upon the tongue. The disintegration time for ODTs generally ranges from several seconds to about a minute. ODTs are designed to disintegrate or dissolve rapidly on contact with saliva, thus eliminating the need to chew the tablet, swallow the intact tablet, or take the tablet with liquids. As with ODDFs in general, this mode of administration can be beneficial to people who require rapid onset of treatment.

In certain embodiments, the fast dissolving property of the ODTs requires quick ingress of water into the tablet matrix. This may be accomplished by maximizing the porous structure of the tablet, incorporation of suitable disintegrating agents and use of highly water-soluble excipients in the formulation. Excipients used in ODTs typically contain at least one superdisintegrant (which can have a mechanism of wicking, swelling or both), a diluent, a lubricant and optionally a swelling agent, sweeteners and flavorings. See, e.g., Nagar et al., Journal of Applied Pharmaceutical Science, 2011; 01 (04):35-45. Superdisintegrants can be classified as synthetic, natural and co-processed. In this context synthetic superdisintegrants can be exemplified by sodium starch glycolate, croscarmellose sodium, cross-linked polyvinylpyrrolidone, low-substituted hydroxypropyl cellulose, microcrystalline cellulose, partially pregelatinized starch, cross-linked alginic acid and modified resin. Natural superdisintegrants can be processed mucilages and gums are obtained from plants and can be exemplified by Lepidium sativum seed mucilage, banana powder, gellan gum, locust bean gum, xanthan gum, guar gum, gum karaya, cassia fistula seed gum, mangifera indica gum, carrageenan, agar from Gelidium amansii and other red algaes, soy polysaccharide and chitosan. Diluents can include, e.g., mannitol, sorbitol, xylitol, calcium carbonate, magnesium carbonate, calcium sulfate, magnesium trisilicate and the like. Lubricants can include, e.g., magnesium stearate and the like. Those skilled in the art are familiar with ODT manufacturing techniques.

Other ODDFs which may be used herein include rapidly dissolving films which are thin oral strips that release medication such as gaboxadol or a pharmaceutically acceptable salt thereof quickly after administration to the oral cavity. The film is placed on a patient's tongue or any other mucosal surface and is instantly wet by saliva whereupon the film rapidly hydrates and dissolves to release the medication. See e.g., Chaturvedi et al., Curr Drug Deliv. 2011 July; 8 (4):373-80. Fastcaps are a rapidly disintegrating drug delivery system based on gelatin capsules. In contrast to conventional hard gelatin capsules, fastcaps consist of a gelation of low bloom strength and various additives to improve the mechanical and dissolution properties of the capsule shell. See, e.g., Ciper and Bodmeier, Int J Pharm. 2005 Oct. 13; 303 (1-2):62-71. Freeze dried (lyophilized) wafers are rapidly disintegrating, thin matrixes that contain a medicinal agent. The wafer or film disintegrates rapidly in the oral cavity and releases drug which dissolves or disperses in the saliva. See, e.g., Boateng et al., Int J Pharm. 2010 Apr. 15; 389 (1-2):24-31. Those skilled in the art are familiar with various techniques utilized to manufacture ODDFs such as freeze drying, spray drying, phase transition processing, melt granulation, sublimation, mass extrusion, cotton candy processing, direct compression, etc. See, e.g., Nagar et al., supra.

When administered, ODDFs containing gaboxadol or a pharmaceutically acceptable salt thereof disintegrate rapidly to release the drug, which dissolves or disperses in the saliva. The drug may be absorbed in the oral cavity, e.g., sublingually, buccally, from the pharynx and esophagus or from other sections of gastrointestinal tract as the saliva travels down. In such cases, bioavailability can be significantly greater than that observed from conventional tablet dosage forms which travel to the stomach or intestines where drug can be released.

Intranasal forms enhance rapid uptake of gaboxadol via the nasal and pulmonary system. Intranasal formulations of therapeutic agents are well known and those skilled in the art may adapt gaboxadol to such a format. Design choices depend on whether the product will be a solution or suspension. Critical parameters include pH and buffer selection, osmolality, viscosity, excipient selection and choice of penetration enhancers or other components to enhance residence time in the nasal cavity. (See DPT Laboratories Ltd publications at www.dptlabs.com).

A desirable target of the invention is to rapidly achieve a blood level of gaboxadol which achieves GABAA receptor saturation in the brain. GABAA receptor saturation level is a blood level greater than about 400, 500, 600, 700, 750, 800, 900 and 1000 ng/ml. Preferably, GABAA receptor saturation is achieved at over 900 ng/ml.

As the dosing of gaboxadol in the present invention is significantly higher in certain embodiments than ever previously attempted, it is anticipated that the pharmacological levels will reach levels different from those previously observed. For example, it is anticipated that the first treatment provides Cmax equal to or greater than about 500, 600, 700, 750, 800 ng/ml, and preferably greater than 900 ng/ml.

Also desireably, plasma Tmax is achieved within 90 minutes the first treatment. More preferably Tmax is achieved at 75, 60, 45 or 30 minutes after first treatment. In certain embodiments, the Tmax of the first treatment is less than 2 hours. In certain embodiments, the Tmax of the first treatment is less than 1.5 hours. In certain embodiments, the Tmax of the first treatment is less than 1 hour. In certain embodiments, the Tmax of the first treatment is about half an hoar.

Alternatively, embodiments provided herein are methods of reducing risk of suicide including administering to a patient in need thereof a pharmaceutical composition including gaboxadol or a pharmaceutically acceptable salt thereof wherein the composition provides an in vivo plasma profile having a AUC0-∞ of greater than about 900 ng*hr/ml. Preferably, the in vivo plasma profile demonstrates an AUC0-2 of greater than about 900 ng*hr/ml and provides rapid onset and durable effect in the patient for more than 3 days after administration.

The inventors have the benefit of public disclosure by others of previous attempts to use gaboxadol as a therapeutic agent. Gaboxadol has been tested in single doses up to about 40 mg in human patient populations. Daily or more frequent maintenance dosing has normally been used. Single doses of gaboxadol have also been employed for understanding pharmacokinetic parameters of drug administration. For example, in publications including WIPO patent application WO2017015049, and Boyle et al. (2009) Hum. Psychopharmacol. Clin. Exp., 24: 61-71 (doi: 10.1002/hup.9860), single oral doses have been analyzed in healthy human subjects only to determine plasma concentration-time profiles, Cmax, Tmax, AUC (area under the curve), PK, PD and other standard pharmacological and psychometric measures which may be calculated by those skilled in the art.

In the method of the invention, if the first treatment comprises two administrations (within the first 12 hours), physicians may advise different forms of gaboxadol to be employed. For example, if the first administration is oral, the second administration is intranasal. Or vice versa. Alternatively both administrations may be of the same form.

Combination Therapy

In certain embodiments, provided herein are methods of reducing risk of suicide and fast-acting relief of depressive symptoms including administering to a patient in need thereof, in addition to the treatment of gaboxadol or pharmaceutically acceptable salt thereof, a second different pharmaceutical composition selected from among ketamine, SAGE-217, tiagabine, clozapine and pharmaceutically acceptable salts thereof. In certain embodiments, the second pharmaceutical composition is administered at the same time as the treatment with gaboxadol.

In certain embodiments, provided herein are methods of reducing risk of suicide including administering to a patient in need thereof a pharmaceutical composition including a first treatment gaboxadol or a pharmaceutically acceptable salt thereof followed by no gaboxadol for 3 or more days, wherein the second pharmaceutical composition may be also administered according to its regularly prescribed schedule and dose or alternatively only at the same time as gaboxadol treatment.

In certain embodiments, the first treatment and/or the second pharmaceutical compositions may be provided in a combined dosage form.

In certain embodiments, in addition to administration of the first pharmaceutical composition the second pharmaceutical composition may provide a synergistic effect to improve at least one symptom of risk of suicide and/or provide a rapid relied of mood symptoms in depression and treatment-resistant depression. In preferred embodiments, the combination therapy demonstrates synergistic effect and employs a dose of gaboxadol and the second pharmaceutical in which one or both compounds are provided a doses known to be individually sub-threshold for therapeutic effect in reducing risk of suicide. As such, in certain embodiments, the invention contemplates a combination therapy wherein the amount of gaboxadol in the first treatment is 30 mg, 25 mg, 20 mg, 1.5 mg, 12 mg, 10 mg or less. In certain embodiments, the amount of ketamine can be about 10, 9, 8, 7, 5, 4, 3, 2,or 1 mg or less.

SAGE-217 is an investigational medication which is under development by SAGE Therapeutics for the treatment of major depressive disorder, postpartum depression, essential tremor, Parkinson's disease, insomnia, and seizures. It is a synthetic, orally active, inhibitory pregnane neurosteroid, and acts as a positive allosteric modulator of the GABAA receptor. The drug was developed as an improvement of allopregnanolone (brexanolone) with high oral bioavailability and a biological half-life suitable for once-daily administration. As of February 2018, SAGE-217 is in phase II clinical trials for major depressive disorder, postpartum depression, essential tremor, and Parkinson's disease and is in phase I clinical studies for insomnia and seizures. It is also in the preclinical stage of development for dyskinesias. The SAGE-217 chemical formula is 3α-Hydroxy-3β-methyl-21-(4-cyano-1H-pyrazol-1'-yl)-19-nor-5β-pregnan-20-one; 3β-Methyl-21-(4-cyano-1H-pyrazol-1'-yl)-19-norpregnanolone; 3α-Hydroxy-3β-methyl-5β-dihydro-21-(4-cyano-1H-pyrazol-1'-yl)-19-norprogesterone.

EXAMPLES

Examples have been set forth below for the purpose of illustration and to describe certain specific embodiments of the invention. However, the scope of the claims is not to be in any way limited by the examples set forth herein. Various changes and modifications to the disclosed embodiments will be apparent to those skilled in the art and such changes and modifications including, without limitation, those relating to the methods of the invention may be made without departing from the spirit of the invention and the scope of the appended claims.

Example 1

Whole-Brain Drug Screening Platform

Many preclinical assays are currently used to try to elucidate or predict the clinical effects of new drugs on the brain. These include in vitro high-content screening (HCS) assays that measure a drug's pharmacokinetics for specific molecular target(s) and its effect(s) in simple cellular assays, in vivo assays that measure global responses at relatively low resolution (PET/CT, PET/MRI, fMRI) or local responses at high, cellular resolution (electrophysiology or two-photon imaging), and behavioral assays that measure animal's performance in various tasks (Jain and Heutink, 2010; Judenhofer et 2008; Markou et al., 2009). Despite a great deal of effort put into preclinical research, the clinical effects of drugs continue to be unpredictable, plaguing the drug development pipeline and resulting in a >90% failure rate in clinical trials (Pammolli et al., 2011).

A unique and novel approach to preclinical testing of psychiatric drugs is based on the proposition that a direct readout of drug-evoked brain activation or inhibition in an animal is the most relevant preclinical assay, because psychiatric drugs exert their effects via activation or inhibition of specific neural circuits and cell types in the brain. Importantly, in contrast to the limitations of existing in vivo methods to measure brain activation, such as PET/CT, PET/MRI and phMRI that suffer from low spatial resolution, or electrophysiology or two-photon imaging that suffer from a limited spatial scope, the new approach enables us to measure drug-evoked brain activation or inhibition across the entire mouse brain at an unprecedented single cell resolution. The method called "pharmacomapping" (implemented by Certerra, Inc. Farmingdale, N.Y.) is based on a largely automated drug-screening platform that comprises whole-brain detection of drug-evoked neuronal activation represented by drug-evoked expression of the immediate early gene (IEG) c-fos (Herrera and Robertson 1996). Until now, the detection of c-fos as a marker of brain activation has been done by laborious methods of in situ hybridization or immunohistochemistry in brain tissue sections, followed by mounting the sections on microscopic slides, manual imaging, and largely visual quantification. Nevertheless, over the last two decades a number of studies used these methods to test drug-evoked activity in the mouse or rat brain for various psychoactive medications, including antipsychotics, antidepressants, stimulants and anxiolytics (Engber et al., 1998; Kiss, 2018; Salminen et al., 1996; SEMBA et al., 1996; Slattery et al., 2005; Sumner et al., 2004). These studies, even though typically assaying only a few brain regions at a time, represent a validation for the concept of using c-fos expression in the rodent brain in psychoactive drug screening (Sumner, Cruise et al. 2004).

Figure 1:
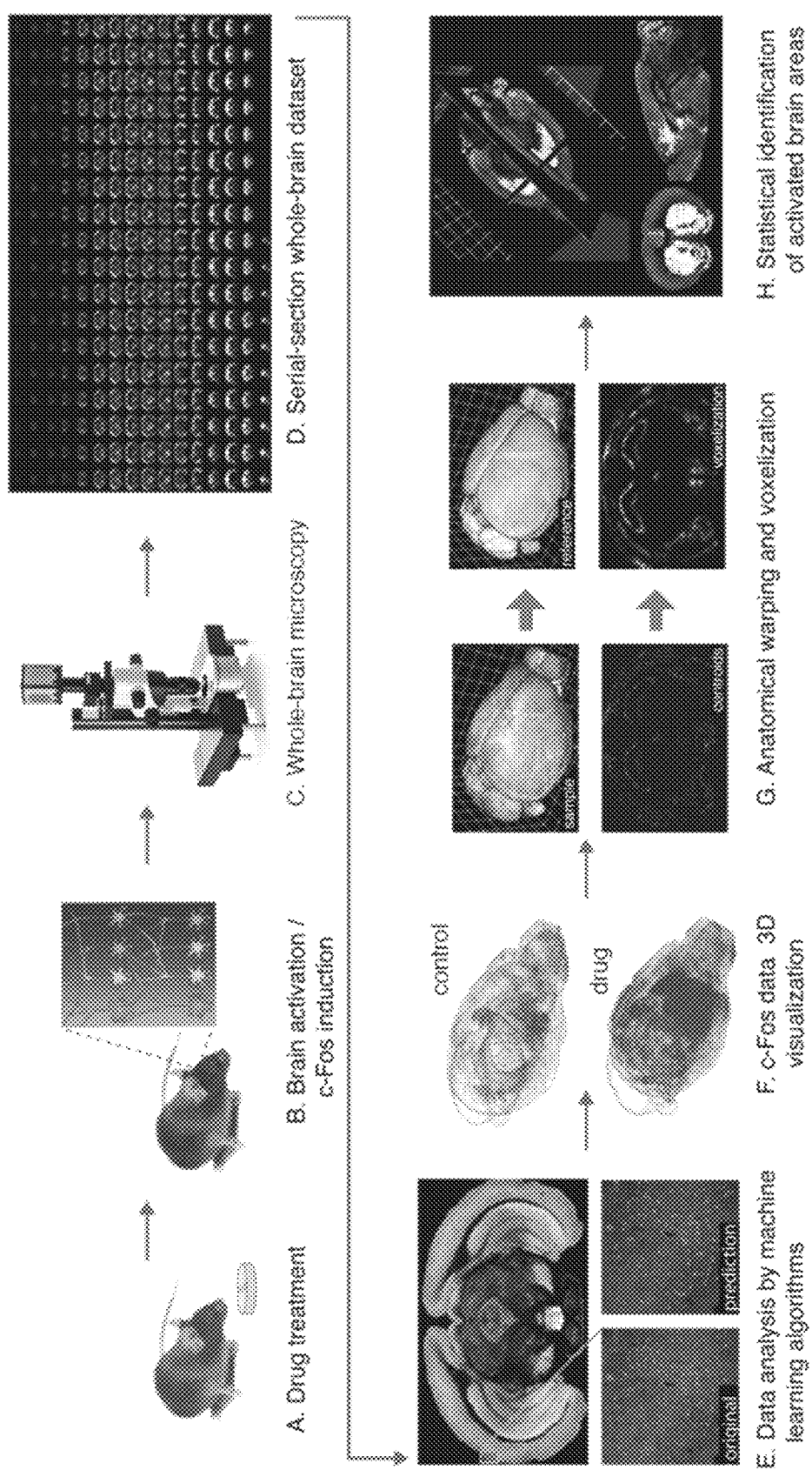
FIG. 1 shows exemplary whole-brain pharmacomaps representing drug-evoked brain activation in the mouse.
(A) Mice are treated with a drug or vehicle solution for the control group using either intraperitoneal (i.p.), per oral (p.o.), subcutaneous (s.c.), intramuscular (i.m.) or intravenous (i.v.) delivery.
(B) This leads to the induction of the immediate early gene c-fos in activated neurons that peaks typically within 1.5 to 3 hrs depending on the drug's pharmacokinetics.
(C) After that period the mice are killed, the c-fos induction is visualized using whole-brain immunostaining, the brains are chemically cleared and finally imaged by light-sheet fluorescent microscopy (LSFM).
(D) The whole-brain scans are represented as serial section datasets typically with XYZ resolution of 4×4×5 microns.
(E) The c-fos+ cells are detected in these datasets using custom trained machine learning algorithms.
(F) The whole-brain distribution of the detected c-fos+ cells is represented in 3D as a spatial snap of centroid points in the 3D space of the mouse brain.
(G) This 3D map distribution is registered to a reference mouse brain and spatially voxelized using overlapping 150-micron sphere voxels.
(H) Finally, the drug-evoked pharmacomap is generated by a statistical comparison of the c-fos+ cell distributions of the drug-treated and control vehicle-treated mice, typically using 6 animals per group.

In contrast to the older methods, the pharmacomapping method uses automated and standardized whole-brain immunostaining and brain clearing together with advanced microscopy (light-sheet fluorescence microscopy, LSFM), computational (e.g. machine learning) and statistical methods (FIG. 1). The first generation of this platform used serial two-photon tomography (STPT) as a method for imaging and c-fos-GFP mice expressing green fluorescent protein (GFP) under the control of the c-fos promoter (US 20140297199A1). The second generation of the pharmacomapping platform currently employed by Certerra uses whole-brain immunostaining and clearing procedure named iDISCO+ and whole-brain imaging by light-sheet fluorescence microscopy to detect c-fos-positive neurons in wild type mice The pharmacomapping platform thus uses the well-established concept of c-fos expression as a cellular marker of neuronal activation and applies it as a standardized and highly quantitative whole-brain assay capable of generating detailed and reproducible drug-evoked whole-brain activation patterns, called pharmacomaps™.

Example 2

Mapping the Brain Activation Underlying the Action of Ketamine as a Fast-Acting Antidepressant Traditional antidepressants, when applied acutely as a single dose chosen to match human equivalent doses used in clinical treatments of depression, evoke a discreet brain activation pattern comprising frontal cortex, the bed nuclei of the stria terminalis (BST), central amygdala (CEA), paraventricular hypothalamus (PVH), paraventricular thalamic nucleus (PVT), and locus coeruleus (LC) (Slattery et al., 2005; Sumner et al., 2004). Recently, intravenous ketamine used acutely at subanesthetic doses was shown to act as a very rapid and robust antidepressant, with a positive therapeutic effect within a few hours instead of the typical two to three weeks that are needed for a therapeutic effect of traditional antidepressants. While this exciting and novel clinical efficacy of ketamine has been reproduced in a number of clinical studies, the mechanism by which ketamine achieves this effect remains largely speculative.

Figure 2:
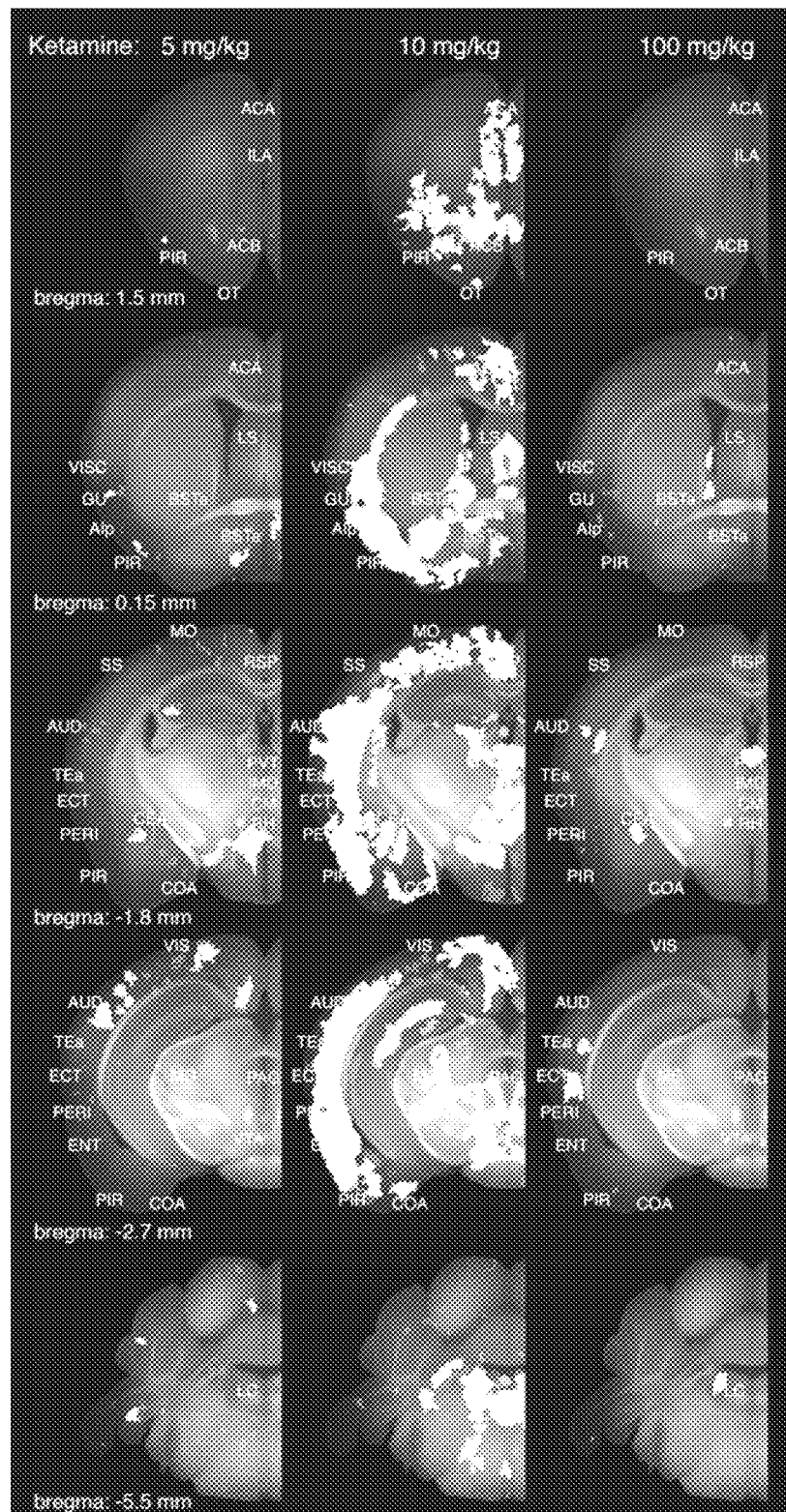
FIG. 2 shows an exemplary ketamine dose-curve pharmacomaps.

Using the pharmacomapping platform, we screened the whole-brain effect of acute single dose ketamine at three doses: 1) 5 mg/kg (human equivalent dose, HED 25 mg) which is below the subanesthetic dose shown to act as a rapid antidepressant; 2) 10 mg/kg (HED 50 mg) which is comparable to the clinical rapid antidepressant dose, 3) 100 mg/kg which is an anesthetic dose not known to have any antidepressant properties. This experiment revealed a striking bell shaped dose-response curve that comprised a modest activation at 5 and 100 mg/kg but a very robust and broad activation comprising many cortical areas and midline thalamic nuclei as well as several other brain structures only at the 10 mg/dose (FIG. 2). This pattern is not only very robust but also unique as it does not match any other patterns from the FDA-approved drugs screen by pharmacomapping to date.

Starting from the rostral part of the brain at bregma 1.5 mm, ketamine at 10 mg/kg (but not at 5 or 100 mg/kg) evoked a prominent activation of the anterior cingulate (ACA), prelimbic (PL) and infralimbic (MA) cortex, as well as piriform cortex (PIR) and the nucleus accumbens of the ventral striatum (ACB) (FIG. 2). Moving caudally, ACA and PIR continue to show a prominent activation by ketamine at 10 mg/kg, and similar activation is seen for the associational visceral (VISC), gustatory (GU), agranular insular (AIp) cortical areas. The lateral septum (LS) and the anterior part of the bed nuclei of the stria terminalis (BSTa) are also activated. At bregma level −1.8 mm, cortical areas continue to show a very broad pattern of activation selectively at 10 mg/kg, including retrosplenial (RSP), motor (MO), somatosensory (SS), auditory (AUD), temporal associational (TEa), perirhinal (PERI) and entorhinal cortex. In addition, midline thalamic nuclei, including the paraventricular nucleus (PVT), intermediodorsal nucleus (IMB), central medial nucleus (CM), and rhomboid nucleus (RH), as well as cortical amygdala and central amygdala (CEA) were also activated. The very broad cortical activation continues further caudally and includes the visual (VIS), ectorhinal (ECT) TEa, AUD, PERI and ENT cortical areas, as well as medial geniculate complex (MG) and the periaqueductal gray (PAG) and the noradrenergic locus coeruleus (LC) (FIG. 2).

Example 3

Discovery of Gaboxadol's Unexpected Potential as a Rapid Antidepressant and Anti-Suicidal Effect The ketamine dose of 10 mg/kg, which evoked broad activation in the pharmacomapping assay, was also shown to have acute positive effect in a number of mouse behavioral studies used to model depression, such as forced swim, tail suspension and learned helplessness. Importantly, the corresponding HED of 50 mg ketamine per 60 kg man, is within the human dose range of 0.5 to 1 mg/kg used to achieve rapid antidepressant effect ever in treatment-resistant patients and alleviate suicidal ideation in clinically depressed patients. Therefore our pharmacomap-based prediction is that the above described 10 mg/kg ketamine-induced activation pattern represents a neuronal circuit-based mechanism of action for ketamine's rapid and dramatic therapeutic effect in depression and suicidal ideation seen in the clinics. Based on this assumption we would also predict that other compounds that evoke a comparable pharmacomap in our assay should also act as rapid antidepressants in the clinics.

This discovery and invention show that gaboxadol at the dose of 10 mg/kg evokes a very similar brain activation as ketamine, providing the first evidence that gaboxadol may in fact act as a rapid antidepressant and anti-suicidal agent. As shown in FIG. 3, the wide cortical activation and to a lesser degree the midline thalamic activation and the activation of midbrain PAG and brainstem LC are very similar between gaboxadol and ketamine, suggesting that gaboxadol at HED 50 mg (60 kg man) may have the same therapeutic efficacy as ketamine in treating depression and suicidal ideation.

What further is striking and worth noting about this discovery is that gaboxadol and ketamine are structurally unrelated molecules and act via two entirely different molecular targets: ketamine is an antagonist at the NMDA type glutamatergic receptors that are an important part of excitatory synaptic transmission in the brain, whereas gaboxadol is an agonist at the δ subunit-containing GABAergic receptors that are an important part of inhibitory synaptic transmission in the brain. Thus, the discovery that gaboxadol evokes brain-wide activation matching the pattern of ketamine is entirely unexpected and could not have been predicted based on previous scientific literature or knowledge. The unexpected nature of the present discovery is also clear from the fact that gaboxadol was most tested by Lundbeck as a sleep medication with the expectation that it would act via the target inhibitory GABA receptors to suppress brain excitation, though it failed for this indication in clinical trials. Similarly, gaboxadol is currently being tested for its ability to suppress abnormally increased brain excitation in two developmental disorders, the Angelman syndrome and Fragile X syndrome (ClinicalTrials.gov Identifier: NCT03697161 and NCT04106557). Thus the believed inhibitory action of gaboxadol is the exact opposite of the present discovery of gaboxadol-evoked broad brain excitation.

Example 4

Synergistic Effect of Gaboxadol and Ketamine

Based on this hypothesis of shared downstream circuits, the data so far show that gaboxadol at 10 mg/kg and ketamine at 10 mg/kg evoked comparable brain activation patterns. As mentioned above, gaboxadol and ketamine act via very different molecular targets, GABA-A receptors and NMDA receptors, respectively, and thus may be expected to initially involve different signaling events. At the same time, the similarity of the evoked activation patterns suggests that the initial compound-specific signaling events lead to a common downstream brain circuit activation.

We next asked whether gaboxadol and ketamine may in fact synergize in their brain activation effects. As shown in FIG. 4, neither gaboxadol at 3 mg/kg nor ketamine at 6 mg/kg alone evoked any brain activation detectable using the assay. However, the combination of gaboxadol at 3 mg/kg + ketamine at 6 mg/kg elicited a clear activation of a number of cortical areas that were also activated by each drug individually when administered at a full dose of 10 mg/kg as described above. These data show that gaboxadol and ketamine can synergize in their brain activation action, establishing that a combination therapy at a sub-threshold dose of each (also called a synergistic dose) is an effective strategy to achieve the desired rapid onset therapeutic effect while avoiding possible side-effects specific for each drug.

Example 5

Gaboxadol and Ketamine Effect in Forced Swim Task

The forced swim test is a frequently used behavioral protocol with a well-established therapeutic predictability for a broad range of antidepressants including ketamine (Porsolt et al. 1977; Cryan and Mombereau 2004; Cryan et al. 2005; Lucki et al. 2001). In this test the mouse is put in a beaker filled with water and the time spent struggling, swimming and floating is measured, with the time spent floating when the mouse stops struggling to swim—being used as a behavioral correlate of depression.

To test whether gaboxadol shows the same behavioral effect as ketamine, the effect of a single dose of ketamine (10 mg/kg) or gaboxadol (10 mg/kg) on forced swim behavior 1 hour and 24 hours after the drug delivery was compared. As shown in FIG. 5, previous results from other groups showing that ketamine at this dose significantly decreases the time the drug treated mice spent floating both at the 1 hour and 24-hour time point compared to a vehicle treated control group was reproduced. Remarkably, the group of mice treated with gaboxadol exhibited a nearly identical behavioral effect as the ketamine group (FIG. 5). This supports the conclusion from the pharmacomap brain activation data shown in FIG. 3 that gaboxadol (10 mg/kg) acts in a comparable way to ketamine (10 mg/kg) and is likely to show similar efficacy for treatment-resistant depression and suicidal ideation.

In summary, the data demonstrated that 1) ketamine (10 mg/kg) acts via an entirely novel way as an antidepressant, evoking a very broad cortical and midline thalamus activation in contrast to traditional antidepressants that evoked a much more restricted brain activation; 2) gaboxadol (10 mg/kg), despite having no structural similarity and acting via different molecular targets evokes a very similar pattern of activation as ketamine; 3) gaboxadol and ketamine synergize in their brain activation effect, 4) in agreement with the brain activation data gaboxadol also shows a nearly identical effect in a forced swim test. Thus, based on this data, gaboxadol may have comparable efficacy in treating depression and suicidal ideation as ketamine.

Other rodent behavior models are commonly used to test neuropsychiatric modulators and may be used to demonstrate the effect of gaboxadol. Standard tests as described in Wang et al (2017) Progress in Neuro-Psychopharmacology and Biological Psychiatry Volume 77, 3 July 2017, Pages 99-109 https://doi.org/10.1016/j.pnpbp.2017.04.008; and by Krishnan and Nestler "Animal Models of Depression: Molecular Perspectives" (in J. J. Hagan (ed.), Molecular and Functional Models in Neuropsychiatry, Current Topics in Behavioral Neurosciences 7, DOI 10.1007/7854_2010_108 ©Springer-Verlag Berlin Heidelberg 2011, published online 12 Jan. 2011) are incorporated herein by reference in their entireties.

Example 6

Plasma Concentration Profiles and Dose Proportionality of Gaboxadol Monohydrate The following Example, cited from US Patent Application Publication 2018098974A1 provides the plasma concentration profiles and dose proportionality of gaboxadol monohydrate following single oral doses ranging from 2.5 to 20 mg. The absolute bioavailability of gaboxadol monohydrate capsules ranging from 2.5 to 20 mg is also assessed.

This study was composed of separate groups of 10 healthy adult subjects (at least 4 of each gender) who participated in a 6-period, double-blind, randomized, crossover study designed to access the dose proportionality and absolute bioavailabilty of 5 single oral doses of gaboxadol across the dose range of 2.5 to 20 mg. The order in which the subjects received the 5 single oral doses of gaboxadol (2.5; 5; 10; 15; and 20 mg) was randomized within Treatment Periods 1 through 5. Each subject was expected to complete all 6 treatment periods and there was a washout of at least 4 days between each treatment period.

Each oral dosing within Treatment Periods consisted of 2 capsules of test drug taken simultaneously at each scheduled dosing. The treatment designations for the orally administered study drugs were as follows:

Treatment A—one 2.5 mg gaboxadol capsule and 1 matching placebo capsule;

Treatment B—one 5 mg gaboxadol capsule and 1 matching placebo capsule;

Treatment C—one 10 mg gaboxadol capsule and 1 matching placebo capsule;

Treatment D—one 15 mg gaboxadol capsule and 1 matching placebo capsule; an

Treatment E—20 mg gaboxadol (two 10 mg gaboxadol capsules).

Subjects received their study drug after an overnight fast with 240 mL of water in the morning about 8:00 AM. Water was permitted ad libitum except within 1 hour prior to and after study drug administration. No food was allowed for 4 hours post dose.

For each subject in each treatment, plasma and urine samples were collected over 16 hours post-dosing for the determination of pharmacokinetic parameters (e.g., AUC, Cmax, Tmax, apparent t1/2, cumulative urinary excretion, renal clearance, clearance, and steady-state volume of distribution, as appropriate). AUC and Cmax for gaboxadol were potency adjusted to facilitate comparison of pharmacokinetic data across studies. Table 1 provides the individual potency-adjusted pharmacokinetic parameters of gaboxadol following single oral doses (2.5, 5, 10, 15, and 20 mg).

The arithmetic mean plasma concentration-time profiles of gaboxadol following single oral doses (2.5, 5, 10, 15, and 20 mg) were calculated. The bioavailability of gaboxadol is approximately 92%. Plasma $AUC_{0-\infty}$ and Cmax of gaboxadol show dose proportional increases and appear to be linear over the entire dose range examined, from of 2.5 to 20 mg. The time to peak plasma concentrations (Tmax 30-60 min) and the half-life (t1/2 of 1.5 h) for gaboxadol appear to be independent of dose across the gaboxadol dose range of 2.5 to 20 mg. The excretion of gaboxadol is mainly via urine, where 96.5% of the dose is recovered; 75% is recovered within 4 hours after administration.

TABLE 1

Pharmacokinetic parameters for gaboxadol following oral and IV administration.
Pharmacokinetic parameters for gaboxadol following oral and IV administration

| Parameter | Geometric Mean (N = 10) | | | | | | |
|---|---|---|---|---|---|---|---|
| | 2.5 mg | 5 mg | 10 mg Oral | 10 mg I.V. | 15 mg | 20 mg | Slope (90% CI)② |
| $AUC_{0-\infty}$ (ng · hr/mL) | 90 | 171 | 346 | 380 | 539 | 669 | 0.98 (0.95, 1.01) |
| $C_{max}$ (ng/mL)† | 61 | 110 | 232 | 212 | 382 | 393 | 0.95 (0.88, 1.02) |
| Tmax (hr)‡ | 0.5 | 0.6 | 0.5 | — | 0.5 | 0.6 | |
| Apparent $t_{1/2}$ (hr)② | 1.5 | 1.5 | 1.6 | 1.5 | 1.5 | 1.6 | |
| CL/F (mL/min)§ | 461 | 488 | 476 | 438 | 469 | 499 | |
| $f_e$ (%) | 43 | 45 | 53 | 53 | 50 | 53 | |
| $CL_R$ (mL/min) | 196 | 222 | 250 | 208 | 234 | 265 | |
| F (%) (90% CI)* | | | | 92% (0.86, 0.97) | | | |

†$C_{max}$ (ng/mL) for 10 mg IV.
‡Median
②Harmonic Mean
§CL/F (mL/min) for 10 mg IV.
②Bioavailability relative to 10 mg I.V. reference based on pooled dose-adjusted (to 10 mg) oral $AUC_{0-\infty}$ values.
②Dose proportionality assessment of oral treatments only
②Indicates text missing or illegible when filed.

Example 7

Pharmacokinetic Comparison al Gaboxadol ODT Formulation to a Gaboxadol Monohydrate Capsule Formulation Pharmacokinetic Comparison of Gaboxadol ODT Formulation to a Gaboxadol Monohydrate Capsule Formulation (Based on disclosure in US patent application publication US2017348232.

The invention contemplates a relatively high dose of gaboxadol administered in a first treatment followed by an extended period of 3 or more days with no further gaboxadol administration. The dose form of gaboxadol is preferably an oral form, and most preferably a tablet, film or wafer which orally disintegrates. Dose forms of the invention may be developed by those skilled in the art, relying on this specification, and particularly by adapting the unit dosage forms disclosed in US2017/348232, set out in this Example. Preferred modifications of this Example will achieve the PK characteristics disclosed and claimed herein, which may include GABAA receptor saturation (blood level greater than about 400, 500, 600, 700, 750, 800, 900 and 1000 ng/ml; Cmax equal to or greater than about 500, 600, 700, 750, 800 ng/ml, and preferably greater than 900 ng/ml; Plasma Tmax achievement within 90 minutes the first treatment (more preferably at 75, 60, 45 or 30 minutes after first treatment); and AUC0-2 of greater than about 900 ng*hr/ml.

Gaboxadol 15 mg Orally Disintegrating Tablet Compendial Unit ("ODT"): The gaboxadol ODT formulation is prepared by blending the active drug, aspartame, peppermint flavor, monoammonium glycyrrhizinate, lactose monohydrate, crospovidone, mannitol and FD&C blue #2 in a suitable diffusional blender until uniform. Magnesium stearate is added and the material is blended. The final lubricated blend is compressed on a tablet press.

This was an open-label, randomized, 2-period, single-dose, balanced crossover study in 24 healthy, young adult male and female subjects (at least 6 of each gender). All subjects received 1 of the 2 different treatments in each study period. Treatment A was a single, oral dose of a 15-mg gaboxadol ODT administered (placed on the tongue) in a fasted state without water. Treatment B was a single, oral dose of a 15-mg gaboxadol monohydrate capsule (described in Example 6) administered in a fasted state with 240 mL of water. Subjects were randomized with respect to treatment order. Following each single oral dose of each formulation, plasma samples for gaboxadol assay were collected up to 16 hours post dose. There was a minimum 4-day washout interval between dosing in each treatment period.

The plasma pharmacokinetic profile (T1/2, Cmax, Tmax AUC0-∞, etc.) of each treatment was measured for all subjects. Blood samples for plasma gaboxadol concentration determination were collected through 16 hours following the administration of study drug in each treatment period. Whole blood samples were collected at the protocol-specified time points into sodium heparin Vacutainer polypropylene tubes and processed for analysis for gaboxadol. The samples were slowly mixed by inversion 6 to 8 times and centrifuged at 1500 g for a minimum of 5 minutes at 4° C. The plasma was separated, transferred to round bottom 4.5-mL NUNC polypropylene tubes, and stored frozen at −70° C. Samples were spun and separated within 30 minutes of sampling. The samples were labeled with computer-generated labels.

Cmax and Tmax were obtained by inspection of the concentration-time data. Actual sampling times were used to determine Tmax. AUC to the last time point was calculated using the linear trapezoidal method for ascending concentrations and the log trapezoidal method for descending concentrations. A linear regression was performed on the log-transformed plasma concentration-time data in the apparent elimination phase to obtain the rate constant of elimination (k). The apparent terminal half-life was calculated using the relationship T1/2=ln(2)/k. AUC0-∞, was estimated as the sum of AUC to the last measured concentration and the extrapolated area given by the quotient of the last measured concentration and k. Cl/F was calculated as the ratio of the dose to AUC0-∞ and $V_z/F$ was calculated as the ratio of Cl/F to k. AUC, Cmax, Cl/F and $V_z/F$ were adjusted based on the assay potency of respective tablet or capsule formulation.

FIG. 6 shows the mean plasma concentrations of gaboxadol following administration of the ODT and monohydrate capsule formulations.

TABLE IV summarizes the potency-adjusted plasma pharmacokinetic parameters (adjusted for assayed potencies of the formulations) of gaboxadol following administration of a 15-mg gaboxadol ODT, or a 15-mg gaboxadol monohydrate capsule.

TABLE IV

Summary of Potency-Adjusted Pharmacokinetic Parameters of GBX Following Administration of 15-mg Single Oral Doses to Healthy Subjects (n = 24)

| Pharmacokinetic Parameter (units) | Geometric Means | | Ratio of Geometric Means (ODT/Monohydrate Capsule) and 90% Confidence Interval | MSE |
|---|---|---|---|---|
| | ODT | Monohydrate Capsule | | |
| $AUC_{0-\infty}$ (ng · hr/ml) | 573 | 560 | 1.02 (1.00, 1.05) | 0.0028 |
| $C_{max}$ (ng/mL) | 336 | 386 | 0.87 (0.77, 0.99) | 0.0645 |
| Tmax§ (hr) | 0.75 | 0.50 | 0.188 (0.000, 0.500) | |
| Apparent $t_{1/2}$ (hr)§ | 1.67 | 1.64 | | |
| CL/F (mL/min) (SD) | 443 (73) | 452 (75) | | |
| $V_z/F$ (L) (SD) | 65 (11) | 65 (12) | | |

†$AUC_{0-\infty}$ and $C_{max}$ statistics based on least squares estimates from ANOVA performed on Natural log-transformed values. CL/F and $V_z/F$ statistics are arithmetic means and SD (standard deviation), median is shown for Tmax, and harmonic mean is shown for apparent terminal $t_{1/2}$.
‡For Tmax, Hodges-Lehmann estimate of the median and 90% CI for treatment difference.
§Not adjusted for potency.
Mean squared error (MSE) from ANOVA model on the natural log scale.

Example 8

Gaboxadol Orally Disintegrating Film

A hydrophilic film-forming agent is made from a graft copolymer having a film-forming block of polyvinyl alcohol (PVA) Kollicoat IR® (marketed by BASF), molecular weight about 45,000 Da, and a polyethylene glycol (PEG) plasticizer. The gelling agent is Gelcarin 379. (commercially available from FMC Biopolymer), a compound of the carrageenan family. Kollicoat IR® is introduced into 70% of the amount of purified water under stirring. Agitation is maintained until dissolution of Kollicoat IR®. Since gas bubbles are generated, the solution may be dissolved under a vacuum or the solution can stand (its viscosity is very low) until the gas is dispersed. Tween 80 is incorporated to the stirred solution and flavorings (condensed licorice extract and essential oil of peppermint) and sweetener (acesulfame potassium) are added. Stirring is continued until complete dissolution of all powder. Gaboxadol is introduced with stirring until it is dispersed in the mixture, then the remaining water (30%) is added. Gelcarin 379® is incorporated into suspension under agitation to prevent the formation of aggregates. The final mixture consists of gaboxadol 6% w/w, Kollicoat IR® 15% w/w, Gelcarin 379® 5% w/w, Tween 80 0.2% w/w, acesulfame potassium 0.05% w/w, flavorings 1.5% w/w, purified water qs. Mixing aliquots are then coated on a polyester backing and dried in a type Lab Dryer Coater (Mathis equipment). The coated surfaces are cut using a manual press in 6 cm2 units, and then manually packaged in sealed bags.

Based on the present invention, those skilled in the art may now adapt this example to produce an oral dosage form of gaboxadol is an orally disintegrating form suitable as a unit dosage form of the invention. Especially preferred is an orally disintegrating form comprising 33 mg to 75 mg gaboxadol, or pharmaceutically acceptable salt thereof.

Example 9

Prospective Assessment of the Efficacy of Gaboxadol in Patients at Risk of Suicide This study is designed to determine whether gaboxadol will lead to an improvement in one or more symptoms of risk of suicide such as suicidal ideation. We conduct a randomized clinical trial of oral gaboxadol compared with intranasal ketamine hydrochloride in patients with major depressive disorder who have clinically significant suicidal ideation, as assessed by score on the Scale for Suicidal Ideation (SSI) (Beck A T, Kovacs M, Weissman A: Assessment of suicidal intention: the Scale for Suicide Ideation. J Consult Clin Psychol 1979; 47:343-352). The primary outcome measure is SSI score 24 hours after administration. Other outcome measures include global depression ratings, clinical ratings during 6-week open follow-up treatment, and safety measures. Intranasal ketamine is a close comparator to oral gaboxadol in intended effect and plasma half-life and pharmacokinetics, but studies must be interpreted in light of ketamine's psychoactivity leading to dissociative effects not found with gaboxadol use. We hypothesized that gaboxadol would produce an equal or greater reduction in suicidal ideation at 24 hours compared with ketamine yet without the dissociative effects of ketamine. The trial is adapted from Murrough et al. (2015) and Grunebaum et a (2017).

Methods a) Participants

Eligible patients are 18-65 years old and have a DSM-IV diagnosis of major depressive disorder, a score >16 on the 17-item Hamilton Depression Rating Scale (HAM-D) (22), and a score >4 on the SSI, which is considered a clinically significant cutoff for suicidal ideation (18, 23, 24). A prospective study of 6,891 psychiatric outpatients (23) found that a baseline SSI score >2 predicted suicide during up to 20 years of follow-up, adjusting for other risk factors. Eligible patients have a voluntary admission to an inpatient research unit, and patients are discharged when assessed as stable and not an imminent safety risk. Exclusion criteria includes unstable medical or neurological illness, significant electrocardiographic abnormality, pregnancy or lactation, current psychosis, history of gaboxadol or ketamine abuse or dependence, other drug or alcohol dependence within the past 6 months, suicidal ideation due to binge substance use or withdrawal, prior ineffective trial of or adverse reaction to gaboxadol or ketamine, daily opioid use greater than 20 mg of oxycodone or equivalent during the 3 days before infusion, a score <25 on the Mini-Mental State Examination (25) for persons <60 years old, lack of capacity to consent, and inadequate understanding of English. There is no exclusion for body mass index or weight. Participants are allowed to continue on stable dosages of current psychiatric medications, except that benzodiazepines are not taken within 24 hours before the infusion. Recruitment is conducted via Internet and local media advertisements and clinician referral. The protocol is approved by the Institutional Review Board, and written informed consent is obtained from all participants.

b) Intervention

Participants are randomly assigned to receive gaboxadol hydrochloride at 0.85 mg/kg (e.g. 50 mg per 60 kg patient; 75 mg per 90 kg patient; 33.3 mg per 40 kg patient as an oral capsule, or ketamine at 0.5 mg/kg in 100 mL normal saline infused over 40 minutes. Blood pressure, heart rate, and respiratory rate are monitored every 5 minutes. A psychiatrist or psychiatric nurse certified in advanced cardiac life support administers the treatment and an anesthesiologist is available for consultation by telephone.

A baseline EEG or MEG may be established in the 30 minutes preceding treatment of the patient. EEG or MEG may continue throughout the treatment, or it may be re-assessed at specific time points, such as 30, 45, 60, 90, 120, 150 or 160 minutes after administration.

If patient examination reveals an insufficient response to gaboxadol treatment observed during the first 160 minutes after administration, by any measure, the treating physician may optionally administer a second administration of gaboxadol. Insufficient response may be defined as an EEG power density increase of less than 30% at the time point 160 minutes after the first administration. Preferably the EEG power density is calculated in the 4.75-8.0 Hz range. Alternatively, insufficient response is a whole head MEG planar gradiometer increase of less +3 in the combined delta, theta and alpha activity at the time point 160 minutes after the first administration. The second administration of gaboxadol is given within 12 hours of the first administration. Insufficient response may also include observable clinical symptoms demonstrating lack of response.

After assessments at 24 hours, participants receive optimized standard clinical pharmacological treatment for 6 months, with weekly research ratings for the first 6 weeks in an uncontrolled follow-up observation.

c) Outcome and Measures

Raters are doctoral- or master's-level psychologists. Diagnoses, including substance abuse or dependence, are made using the Structured Clinical interviews for DSM-IV axis I and II disorders (SCID I and II) (26, 27) in a weekly consensus conference of research psychologists and psychiatrists. Suicidal ideation due to binge substance abuse is assessed by clinical history, and past antidepressant trials and current medications are inventoried with our baseline clinical-demographic form, which surveys a range of variables not captured by other instruments. Videotaped assessments are used for weekly reliability monitoring. Intraclass correlation coefficients for key clinical ratings were 0.94 for the SCID 1, 0.96 for the HAM-D, and 0.98 for the SSI. The clinician-rated SSI assessed current severity of suicidal ideation with 19 items scaled from 0 (least severe) to 2 (most severe) (20), items probe wish to die, passive and active suicide attempt thoughts, duration and frequency of ideation, sense of control, deterrents, and preparatory behavior for an attempt (23). The SSI has moderately high internal consistency and good concurrent and discriminant validity (28). It is administered at screening, at baseline within 24 hours before infusion, at 230 minutes after infusion, at 24 hours after infusion, and at weeks 1-6 of follow-up. For brevity we use "day 1" to refer to the 24-hour treatment assessment. Depressive symptoms are assessed with the 17- and 24-item HAM-D (22), the Beck Depression Inventory (BDI) (29), and the Profile of Mood States (POMS) (30). Anxiety is measured with a 5-point Likert scale asking patients to self-rate from 0 (not at all) to 4 (extremely anxious). Adverse effects are measured with the Systematic Assessment for Treatment Emergent Events—General inquiry (31), the Clinician-Administered Dissociative States Scale (CADSS; score range, 0-92) (32), and the positive symptom subscale of the Brief Psychiatric Rating Scale (BPRS), which includes conceptual disorganization, grandiosity, hallucination, and delusions (subscale score range, 0-24) (33). Efficacy ratings and the CADSS and BPRS positive symptom subscale (at baseline, at 230 minutes, and at day 1) are collected by psychologist raters who are not present during the treatment. Administration of the immediate post-treatment CADSS and BPRS positive symptom subscale and all adverse effect ratings are done by the physician who supervises the infusion. Participants are asked at 3 and 6 months about post-study gaboxadol use.

a) Randomization and Blinding

A permuted, blocked design is used, with 1:1 assignment between treatments and block size randomized between 4 and 6 with equal probability. Randomization is stratified on two baseline factors: whether the patient was taking psychiatric medication (yes/no), and whether the patient's baseline SSI score is <8 or >8. The latter stratification factor, based on median baseline SSI score in a previous clinical trial in suicidal depressed patients (34), is to increase the likelihood that the treatment groups are similar in baseline SSI severity. Patients and study personnel are blind to treatment. To assess the adequacy of the blind, patients and raters are asked in the day 1 ratings whether they thought the infusion is ketamine or gaboxadol or if they have "no idea." Treatment response is defined as a day 1 SSI score >50% below baseline. We define remission more stringently as a day 1 SSI score >50% below baseline and less than the eligibility threshold of 4. A remission level of improvement is defined to ensure that the ketamine group has every opportunity to receive gaboxadol. Non-remitters are unblinded, and those who have received ketamine are offered an open gaboxadol infusion, usually the following day. Preexisting medications are held constant from pre-infusion baseline until completion of day 1 ratings after the final infusion. Remitters remain blind and receive a letter from the pharmacy after completing follow-up treatment informing them of their randomized drug.

e) Statistical Analysis

The study is powered assuming a two-sided test of the group effect at an alpha level of 0.05. Effect size estimates, standard deviations, and correlations are based on previous reports (15, 34). A planned sample size of 70, assigned 1:1 to each treatment, provides >80% power to detect a 25% reduction in SSI score over 24 hours in the gaboxadol group and none in the ketamine group. The actual sample size is about 80. Histograms and residual plots of outcomes are inspected for normality. Group comparisons on baseline characteristics are made using the chi-square test or Fisher's exact test as appropriate for categorical variables and the two-sample t test for continuous variables. The modified intent-to-treat analysis includes all randomized participants who are assessed for the primary outcome measure, SSI score at day 1 (N=80). The primary hypothesis is tested using an analysis of covariance (ANCOVA) model of the change in SSI score from baseline to day 1, with treatment group and baseline SSI score as the predictors. Randomization stratum (taking or not taking psychiatric medication), by definition not associated with treatment group, is not associated with the primary outcome measure (p=0.84) and so is not included in the model. Effect size calculations used Cohen's d and number needed to treat. Cohen's d is calculated as the difference in mean group change divided by the standard deviation of baseline values for the whole sample. Secondary analyses use ANCOVA models to test for differential change between groups in SSI score and depressive symptom ratings (the 17- and 24-item HAM-D, the BDI, and the POMS) from baseline to 230 minutes and in depressive symptom ratings from baseline to day 1. Response is compared by drug using logistic regression. Linear regression is used in an exploratory analysis of treatment effects on the suicidal desire/ideation and planning subscales of the SSI (35). Mediation analyses are performed using a structural equation modeling framework in Mplus, version 7 (36). Paired t tests are used to determine whether the participants assigned to ketamine who received an open gaboxadol treatment after day 1 (N=35) experience significant subsequent change in SSI or HAM-D scores. For the longitudinal data analysis, mixed-effects linear regression of SSI and 17-item HAM-D scores over the 6-week follow-up period are used to test for significant change from baseline across the entire sample, regardless of treatment group, since 35 of 40 patients in the ketamine group are non-remitters and receive a subsequent open gaboxadol infusion. Safety analyses include univariate tests comparing infusion-related cardiorespiratory effects, adverse events, and postinfusion severity of positive, dissociative, and anxiety symptom ratings between groups. SAS, version 9.4 (SAS Institute, Cary, N.C.), and SPSS, version 23 (IBM, Armonk, N.Y.), are used for the analyses.

f) Results

Primary Outcome Measure: Day 1 Suicidal Ideation The average SSI score at day 1 lower in the gaboxadol group compared with the ketamine group. Cohen's d for the difference in mean group change demonstrates a greater than medium effect size. Including baseline borderline personality disorder diagnosis as a covariate has little effect on the results)

g) Secondary Outcome Measures

Suicidal ideation. The proportion of responders on the SSI at day 1 was significantly higher in the gaboxadol group than the ketamine group. The decrease in suicidal ideation at 230 minutes after the infusion is greater in the gaboxadol group compared with the ketamine group.

Depressive symptoms. The day 1 TOMS total mood disturbance score shows greater improvement in the gaboxadol group compared with the ketamine group, as do scores on the depression subscale.

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

Those skilled in the art will recognize or be able to ascertain using no more than routine experimentation, many equivalents to the specific embodiments described herein. Such equivalents are intended to be encompassed by the claims.

What is claimed is:

1. A method for achieving relief of depressive symptoms in a patient diagnosed with major depressive disorder or treatment-resistant depression comprising
providing a first treatment of gaboxadol, or pharmaceutically acceptable salt thereof, to a patient in need thereof in an amount sufficient to rapidly alleviate depressive symptoms, and
providing at least one additional treatment of gaboxadol, or pharmaceutically acceptable salt thereof, after a wash-out period of at least 48 hours after the first treatment.

2. The method of claim 1, wherein the additional treatment of gaboxadol, or pharmaceutically acceptable salt thereof, is provided every 3, 4, 5, 6 or 7 days or more after the first treatment.

3. The method of claim 1 wherein the first treatment comprises providing an initial administration of gaboxadol, or pharmaceutically acceptable salt thereof, and a second administration of gaboxadol, or pharmaceutically acceptable salt thereof, within less than 12 hours after the initial administration.

4. The method of claim 3, wherein the second administration of gaboxadol, or pharmaceutically acceptable salt thereof, is provided if a neurological test of the patient demonstrates an insufficient response after about 120, about 160 or about 180 minutes after the initial administration.

5. The method of claim 4, wherein the insufficient response is an electroencephalogram (EEG) power density increase of less than 30% over baseline after about 120, about 160 or about 180 minutes after the first initial administration.

6. The method of claim 5, wherein the electroencephalogram (EEG) power density is calculated in a 0.25-8.0 Hz range.

7. The method of claim 5, wherein the electroencephalogram (EEG) power density is calculated in a 4.75-8.0 Hz range.

8. The method of claim 4, wherein the insufficient response is a whole head magnetoencephalography (MEG) planar gradiometer increase of less than +3 in a combined delta, theta and alpha activity after about 120, about 160 or about 180 minutes after the initial administration.

9. The method of claim 1, wherein the method provides improvement in at least one symptom of risk of suicide selected from the group consisting of suicidal ideation, acute suicidality, recurrent thoughts of death, actions towards suicide and/or suicide attempts.

10. The method of claim 1, wherein the patient is further diagnosed with a condition selected from among suicidal ideation, acute suicidality, risk of self-harm and/or treatment-resistant depression.

11. The method of claim 1, wherein the patient has not been previously treated with, or is not currently being treated with, or is not responding to, an ant-depressive treatment.

12. The method of claim 1, wherein the first treatment comprises about 1 mg to about 300 mg gaboxadol or a pharmaceutically acceptable salt thereof.

13. The method of claim 1, wherein the first treatment comprises about 33 mg to about 300 mg gaboxadol or a pharmaceutically acceptable salt thereof.

14. The method of claim 1, wherein the first treatment comprises about 50 mg to about 300 mg gaboxadol or a pharmaceutically acceptable salt thereof.

15. The method of claim 1, wherein the first treatment is provided in an oral dosage form.

16. The method of claim 15, wherein the oral dosage form is an orally disintegrating form.

17. The method of claim 1, wherein the first treatment is provided intranasally.

18. The method of claim 1, wherein the first treatment of gaboxadol, or pharmaceutically acceptable salt thereof, results in a blood level that exceeds a $GABA_A$ receptor saturation level.

19. The method of claim 18, wherein the $GABA_A$ receptor saturation level is a blood level greater than 900 ng/ml.

20. The method of claim 1, wherein a patient's plasma level of gaboxadol achieves $AUC_{0-2}$ of greater than about 900 ng*hr/ml after the first treatment.

21. The method of claim 20, wherein a plasma $T_{max}$ of gaboxadol is achieved within 45 minutes after administration of the first treatment.

22. The method of claim 1, further comprising providing to the patient, before, after or concurrently with the first treatment, any one of ketamine, SAGE-217, allopregnanolone, ganaxolone, alfadolone, alfaxolone, hydroxydione, minaxolone, pregnanolone, renanolone, AV-101 (L-4-Chlorokynurenine), rapastinel (GLYX-13), MGS0039, LY-341,495, MK-801 (dizocilpine), Ro 25-6981, rislenemdaz (CERC-301, MK-0657), apimostinel (NRX-1074), lanicemine (AZD6765), traxoprodil (CP-101606), (2R,6R)-hydroxynorketamine, decoglurant (INN) (RG1578, RO4995819), memantine, tiagabine, clozapine, [2-amino-4-(2,4,6-trimethylbenzylamino)-phenyl]-carbamic acid ethyl ester (AA29504) and pharmaceutically acceptable salts thereof.

23. The method of claim 1, wherein the first treatment comprises providing concurrently a synergistic dose of gaboxadol, or pharmaceutically acceptable salt thereof, together with a synergistic dose of ketamine.

24. The method of claim 23, wherein the synergistic dose of gaboxadol, or pharmaceutically acceptable salt thereof, is about 20 mg or less.

25. The method of claim 23, wherein the synergistic dose of ketamine is about 10 mg or less.

26. The method of claim 1, further comprising providing to the patient, before, after or concurrently with the first treatment, a pregnane neurosteriod or a pharmaceutically acceptable salt thereof.

27. The method of claim 3 wherein the second administration is provided within less than 6 hours after the initial administration.

28. The method of claim 3 wherein the initial administration of gaboxadol is 50 mg.

29. The method of claim 1, wherein the method provides improvement in at least one symptom of major depressive disorder or treatment-resistant depression as measured in a test selected from the group consisting of global depression rating, HAM-D, the Beck Depression Inventory, and the Profile of Mood States.

30. A method for reducing a risk of suicide in a patient diagnosed as being at risk of suicide comprising;
providing a first treatment of gaboxadol, or pharmaceutically acceptable salt thereof, to a patient in need thereof in an amount sufficient to reduce the risk of suicide, and, providing at least one additional treatment of gaboxadol, or pharmaceutically acceptable salt thereof, after a wash-out period of at least 48 hours after the first treatment.

31. The method of claim 30, wherein the additional treatment of gaboxadol, or pharmaceutically acceptable salt thereof, is provided every 3, 4, 5, 6 or 7 days or more after the first treatment.

32. The method of claim 30 wherein the first treatment comprises providing an initial administration of gaboxadol, or a pharmaceutically acceptable salt thereof, and a second administration a second administration of gaboxadol, or pharmaceutically acceptable salt thereof, within less than 12 hours after the initial administration.

33. The method of claim 32 wherein the second administration is provided within less than 6 hours after the initial administration.

34. The method of claim 33, wherein the second administration of gaboxadol, or pharmaceutically acceptable salt thereof, is provided if a neurological test of the patient demonstrates an insufficient response after about 120, about 160 or about 180 minutes after the initial administration.

35. The method of claim 34, wherein the insufficient response is an electroencephalogram (EEG) power density increase of less than 30% over baseline about 120, about 160 or about 180 minutes after the initial administration.

36. The method of claim 35, wherein the electroencephalogram (EEG) power density is calculated in a 0.25-8.0 Hz range.

37. The method of claim 35, wherein the electroencephalogram (EEG) power density is calculated in a 4.75-8.0 Hz range.

38. The method of claim 34, wherein the insufficient response is a whole head magnetoencephalography (MEG) planar gradiometer increase of less than +3 in a combined delta, theta and alpha activity after about 120, about 160 or about 180 minutes after the initial administration.

39. The method of claim 30, wherein the method provides improvement in at least one symptom of risk of suicide selected from the group consisting of suicidal ideation, acute suicidality, recurrent thoughts of death, actions towards suicide and/or suicide attempts.

40. The method of claim 30, wherein the patient is further diagnosed with a condition selected from among suicidal ideation, acute suicidality, risk of self-harm, major depressive disorder or treatment-resistant depression.

41. The method of claim 30, wherein the patient has not been previously treated with, or is not currently being treated with, or is not responding to, a treatment for being at risk of suicide.

42. The method of claim 30, wherein the first treatment comprises about 1 mg to about 300 mg gaboxadol or a pharmaceutically acceptable salt thereof.

43. The method of claim 30, wherein the first treatment comprises about 33 mg to about 300 mg gaboxadol or a pharmaceutically acceptable salt thereof.

44. The method of claim 30, wherein the first treatment comprises about 50 mg to about 300 mg gaboxadol or a pharmaceutically acceptable salt thereof.

45. The method of claim 30, wherein the first treatment is provided in an oral dosage form.

46. The method of claim 45, wherein the oral dosage form is an orally disintegrating form.

47. The method of claim 30, wherein the first treatment is provided intranasally.

48. The method of claim 30, wherein the first treatment of gaboxadol, or pharmaceutically acceptable salt thereof, results in a blood level that exceeds a $GABA_A$ receptor saturation level.

49. The method of claim 48, wherein the GABAA receptor saturation level is a blood level greater than 900 ng/ml.

50. The method of claim 30, wherein a patient's plasma level of gaboxadol achieves $AUC_{0-2}$ of greater than about 900 ng*hr/ml after the first treatment.

51. The method of claim 50, wherein a plasma $T_{max}$ of gaboxadol is achieved within 45 minutes after administration of the first treatment.

52. The method of claim 30, further comprising providing to the patient, before, after or concurrently with the first treatment, any one of ketamine, SAGE-217, allopregnanolone, ganaxolone, alfadolone, alfaxolone, hydroxydione, minaxolone, pregnanolone, renanolone, AV-101 (L-4-Chlorokynurenine), rapastinel (GLYX-13), MGS0039, LY-341,495, MK-801 (dizocilpine), Ro 25-6981, rislenemdaz (CERC-301, MK-0657), apimostinel (NRX-1074), lanicemine (AZD6765), traxoprodil (CP-101606), (2R,6R)-hydroxynorketamine, decoglurant (INN) (RG1578, RO4995819), memantine, tiagabine, clozapine, [2-amino-4-(2,4,6-trimethylbenzylamino)-phenyl]-carbamic acid ethyl ester (AA29504) and pharmaceutically acceptable salts thereof.

53. The method of claim 30, further comprising providing to the patient, before, after or concurrently with the first treatment, a pregnane neurosteroid or a pharmaceutically acceptable salt thereof.

54. The method of claim 30, wherein the first treatment comprises concurrently providing a synergistic dose of gaboxadol, or pharmaceutically acceptable salt thereof, together with a synergistic dose of ketamine.

55. The method of claim 54, wherein the synergistic dose of gaboxadol, or pharmaceutically acceptable salt thereof, is about 20 mg or less.

56. The method of claim 54, wherein the synergistic dose of ketamine is about 10 mg or less.

57. The method of claim 30 wherein the initial administration of gaboxadol is 50 mg.

58. A method for achieving relief of depressive symptoms in a patient diagnosed with major depressive disorder or treatment-resistant depression comprising;
providing a first treatment of gaboxadol, or pharmaceutically acceptable salt thereof, to a patient in need thereof, in an amount sufficient to alleviate depressive symptoms, and providing at least one additional treatment of gaboxadol, or pharmaceutically acceptable salt thereof, after a wash-out period of at least 3 days after the first treatment.

\* \* \* \* \*

UNITED STATES PATENT AND TRADEMARK OFFICE
CERTIFICATE OF CORRECTION

PATENT NO. : 11,123,332 B2
APPLICATION NO. : 16/691049
DATED : September 21, 2021
INVENTOR(S) : Pavel Osten et al.

Page 1 of 2

It is certified that error appears in the above-identified patent and that said Letters Patent is hereby corrected as shown below:

In the Specification

In Column 2, Line 11, replace "entirety. A" with --entirety.) A--;

In Column 5, Line 41, replace "2 mg, about 1 mg" with --2 mg, or about 1 mg--;

In Column 5, Line 45, replace "2 mg, about 1 mg" with --2 mg, or about 1 mg--;

In Column 7, Line 9, replace "right panel." with --right panel).--;

In Column 10, Line 40, replace "reveals of the drug's" with --reveals the drug's--;

In Column 12, Line 16-17, replace "An example is may" with --An example may--;

In Column 12, Line 29, replace "suicidality et al. (2015)" with --suicidality (Lee et al. (2015)--;

In Column 13, Lines 45-46, replace "compositions of including" with --compositions including--;

In Column 16, Line 5, replace "WO2002094225 WO" with --WO2002094225, and WO--;

In Column 17, Line 17, replace "An biomarker" with --A biomarker--;

In Column 18, Line 14, replace "folio rig" with --following--;

In Column 22, Line 28, replace "2,or 1 mg" with --2, or 1 mg--;

In the Claims

In Column 36, Line 42, Claim 26, replace "neurosteriod" with --neurosteroid--;

Signed and Sealed this
Tenth Day of May, 2022

Katherine Kelly Vidal
*Director of the United States Patent and Trademark Office*

In Column 36, Line 56, Claim 30, replace "comprising;" with --comprising--;

In Column 37, Line 3, Claim 32, replace "and_a" with --and a--;

In Column 38, Line 7, Claim 49, replace "GABAA" with --GABA$_A$--;

In Column 38, Line 46, Claim 58, replace "comprising;" with --comprising--.